(12) United States Patent
Keyer et al.

(10) Patent No.: US 10,898,234 B2
(45) Date of Patent: *Jan. 26, 2021

(54) POLYAXIAL BONE FIXATION ELEMENT

(71) Applicant: DePuy Synthes Products, Inc., Raynham, MA (US)

(72) Inventors: Thomas Keyer, West Chester, PA (US); Joseph Capozzoli, Mount Laurel, NJ (US); Eric McDivitt, Schwenksville, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/172,995

(22) Filed: Oct. 29, 2018

(65) Prior Publication Data

US 2019/0059953 A1 Feb. 28, 2019

Related U.S. Application Data

(63) Continuation of application No. 15/254,382, filed on Sep. 1, 2016, now Pat. No. 10,136,923, which is a (Continued)

(51) Int. Cl.
| A61B 17/70 | (2006.01) |
| A61B 17/88 | (2006.01) |
| A61B 17/86 | (2006.01) |

(52) U.S. Cl.
CPC ...... *A61B 17/7037* (2013.01); *A61B 17/7076* (2013.01); *A61B 17/7077* (2013.01);
(Continued)

(58) Field of Classification Search
CPC ............ A61B 17/7034; A61B 17/7035; A61B 17/7037; A61B 17/7032
See application file for complete search history.

(56) References Cited

U.S. PATENT DOCUMENTS

| 405,546 A | 6/1889 | Frist |
| 513,630 A | 1/1894 | Beard |
| (Continued) |

FOREIGN PATENT DOCUMENTS

| CA | 2289629 A1 | 11/1998 |
| CM | 101249017 A | 8/2008 |
| (Continued) |

OTHER PUBLICATIONS

U.S. Provisional Application Filed on Jun. 17, 2009 by Albert Montello et. al., entitled Top-Loading Polyaxial Construct Extender for Spinal Surgery, U.S. Appl. No. 61/187,902.

(Continued)

*Primary Examiner* — Julianna N Harvey
(74) *Attorney, Agent, or Firm* — BakerHostetler

(57) ABSTRACT

The present disclosure includes a polyaxial bone fixation element for use in spinal fixation to interconnect a longitudinal spinal rod with a patient's vertebra. The polyaxial bone fixation element preferably includes a bone anchor, a collet, a body, and a locking cap. The polyaxial bone fixation element preferably enables in-situ assembly. That is, the polyaxial bone fixation element is preferably configured so that in use, the bone anchor may be secured to the patient's vertebra prior to being received within the body. Accordingly, the polyaxial bone fixation element enables a surgeon to implant the bone anchor without the body to maximize visibility and access around the anchoring site. Once the bone anchor has been secured to the patient's vertebra, the body can be snapped-onto the bone anchor. The bone anchor preferably also includes a second tool interface so that a surgical instrument can be directly coupled to the bone anchor.

20 Claims, 13 Drawing Sheets

Related U.S. Application Data continuation of application No. 14/163,482, filed on Jan. 24, 2014, now Pat. No. 9,439,681, which is a continuation of application No. 12/669,224, filed as application No. PCT/US2008/070670 on Jul. 21, 2008, now Pat. No. 8,663,298.

(60) Provisional application No. 60/988,584, filed on Nov. 16, 2007, provisional application No. 60/950,995, filed on Jul. 20, 2007.

(52) U.S. Cl.
CPC ........ *A61B 17/7082* (2013.01); *A61B 17/864* (2013.01); *A61B 17/8841* (2013.01)

(56) References Cited

U.S. PATENT DOCUMENTS

| | | |
|---|---|---|
| 527,678 A | 10/1894 | Francis |
| 802,896 A | 10/1905 | Webb |
| 2,005,348 A | 6/1935 | Michell |
| 2,338,659 A | 1/1944 | Morehouse |
| 2,396,925 A | 3/1946 | Morehouse |
| 3,173,987 A | 3/1965 | Potruch |
| 3,463,427 A | 8/1969 | Fisher |
| 4,447,934 A | 5/1984 | Anscher |
| 4,601,491 A | 7/1986 | Bell et al. |
| 4,719,905 A | 1/1988 | Steffee |
| 4,805,602 A | 2/1989 | Puno et al. |
| 4,846,614 A | 7/1989 | Steinbock |
| 4,863,383 A | 9/1989 | Grafelmann |
| 4,936,851 A | 6/1990 | Fox et al. |
| 4,944,475 A | 7/1990 | Ono et al. |
| 4,946,458 A | 8/1990 | Harms et al. |
| 5,005,562 A | 4/1991 | Cotrel |
| 5,116,337 A | 5/1992 | Johnson |
| 5,129,388 A | 7/1992 | Vignaud et al. |
| 5,207,678 A | 5/1993 | Harms et al. |
| 5,242,446 A | 9/1993 | Steffee et al. |
| 5,270,678 A | 12/1993 | Gambut et al. |
| 5,282,825 A | 2/1994 | Muck et al. |
| 5,304,178 A | 4/1994 | Stahurski |
| 5,306,275 A | 4/1994 | Bryan |
| 5,306,285 A | 4/1994 | Miller et al. |
| 5,312,410 A | 5/1994 | Miller et al. |
| 5,360,431 A | 11/1994 | Puno et al. |
| 5,383,882 A | 1/1995 | Buess et al. |
| 5,395,374 A | 3/1995 | Miller et al. |
| 5,413,576 A | 5/1995 | Rivard |
| 5,413,602 A | 5/1995 | Metz-Stavenhagen |
| 5,417,684 A | 5/1995 | Jackson et al. |
| 5,443,467 A | 8/1995 | Biedermann et al. |
| 5,449,361 A | 9/1995 | Preissman |
| 5,466,237 A | 11/1995 | Byrd et al. |
| 5,468,241 A | 11/1995 | Metz-Stavenhagen et al. |
| 5,474,555 A | 12/1995 | Puno et al. |
| 5,476,464 A | 12/1995 | Metz-Stavenhagen et al. |
| 5,486,174 A | 1/1996 | Fournet-Fayard et al. |
| 5,496,321 A | 3/1996 | Puno et al. |
| 5,498,262 A | 3/1996 | Bryan |
| 5,501,684 A | 3/1996 | Schlapfer et al. |
| 5,520,689 A | 5/1996 | Schlaepfer et al. |
| 5,520,690 A | 5/1996 | Errico et al. |
| 5,527,183 A | 6/1996 | O'Brien |
| 5,531,746 A | 7/1996 | Errico et al. |
| 5,534,001 A | 7/1996 | Schlapfer et al. |
| 5,536,268 A | 7/1996 | Griss |
| 5,536,270 A | 7/1996 | Songer et al. |
| 5,540,698 A | 7/1996 | Preissman |
| 5,549,608 A | 8/1996 | Errico et al. |
| 5,549,677 A | 8/1996 | Duerr et al. |
| 5,554,157 A | 9/1996 | Errico et al. |
| 5,562,661 A | 10/1996 | Yoshimi et al. |
| 5,575,792 A | 11/1996 | Errico et al. |
| 5,578,033 A | 11/1996 | Errico et al. |
| 5,584,832 A | 12/1996 | Schlaepfer |
| 5,584,834 A | 12/1996 | Errico et al. |
| 5,586,984 A | 12/1996 | Errico et al. |
| 5,601,261 A | 2/1997 | Koike |
| 5,601,429 A | 2/1997 | Blacklock |
| 5,605,457 A | 2/1997 | Bailey et al. |
| 5,605,458 A | 2/1997 | Bailey et al. |
| 5,607,304 A | 3/1997 | Bailey et al. |
| 5,607,426 A | 3/1997 | Ralph et al. |
| 5,609,593 A | 3/1997 | Errico et al. |
| 5,609,594 A | 3/1997 | Errico et al. |
| 5,624,442 A | 4/1997 | Mellinger et al. |
| 5,643,260 A | 7/1997 | Doherty |
| 5,643,262 A | 7/1997 | Metz-Stavenhagen et al. |
| 5,643,265 A | 7/1997 | Errico et al. |
| 5,645,544 A | 7/1997 | Tai et al. |
| 5,647,873 A | 7/1997 | Errico et al. |
| 5,662,651 A | 9/1997 | Tornier et al. |
| 5,667,508 A | 9/1997 | Errico et al. |
| 5,669,911 A | 9/1997 | Errico et al. |
| 5,672,175 A | 9/1997 | Martin |
| 5,683,390 A | 11/1997 | Metz-Stavenhagen et al. |
| 5,683,392 A | 11/1997 | Richelsoph et al. |
| 5,683,404 A | 11/1997 | Johnson |
| 5,688,273 A | 11/1997 | Errico et al. |
| 5,690,630 A | 11/1997 | Errico et al. |
| 5,694,760 A | 12/1997 | Baxter |
| 5,704,939 A | 1/1998 | Justin |
| 5,725,582 A | 3/1998 | Bevan et al. |
| 5,725,588 A | 3/1998 | Errico et al. |
| 5,728,098 A | 3/1998 | Sherman et al. |
| 5,733,285 A | 3/1998 | Errico et al. |
| 5,738,685 A | 4/1998 | Halm et al. |
| 5,772,663 A | 6/1998 | Whiteside et al. |
| 5,782,831 A | 7/1998 | Sherman et al. |
| 5,782,833 A | 7/1998 | Haider |
| 5,797,911 A | 8/1998 | Sherman et al. |
| 5,810,818 A | 9/1998 | Errico et al. |
| 5,817,094 A | 10/1998 | Errico et al. |
| 5,860,987 A | 1/1999 | Ratcliff et al. |
| 5,863,293 A | 1/1999 | Richelsoph |
| 5,868,748 A | 2/1999 | Burke |
| 5,876,402 A | 3/1999 | Errico et al. |
| 5,879,350 A | 3/1999 | Sherman et al. |
| 5,882,350 A | 3/1999 | Ralph et al. |
| 5,885,286 A | 3/1999 | Sherman et al. |
| 5,888,204 A | 3/1999 | Ralph et al. |
| 5,891,145 A | 4/1999 | Morrison et al. |
| 5,899,940 A | 5/1999 | Carchidi et al. |
| 5,902,305 A | 5/1999 | Beger et al. |
| 5,938,663 A | 8/1999 | Petreto |
| 5,951,287 A | 9/1999 | Hawkinson |
| 5,961,329 A | 10/1999 | Stucki-McCormick |
| 5,964,760 A | 10/1999 | Richelsoph |
| 6,001,098 A | 12/1999 | Metz-Stavenhagen et al. |
| 6,010,503 A | 1/2000 | Richelsoph et al. |
| 6,015,409 A | 1/2000 | Jackson |
| 6,017,177 A | 1/2000 | Lanham |
| 6,019,760 A | 2/2000 | Metz-Stavenhagen et al. |
| 6,022,350 A | 2/2000 | Ganem |
| 6,053,917 A | 4/2000 | Sherman et al. |
| 6,063,090 A | 5/2000 | Schlaepfer |
| 6,074,391 A | 6/2000 | Metz-Stavenhagen et al. |
| 6,077,262 A | 6/2000 | Schlaepfer et al. |
| 6,077,263 A | 6/2000 | Ameil et al. |
| 6,083,224 A | 7/2000 | Gertzbein et al. |
| 6,090,110 A | 7/2000 | Metz-Stavenhagen |
| 6,126,662 A | 10/2000 | Carmichael et al. |
| 6,132,432 A | 10/2000 | Richelsoph |
| 6,183,472 B1 | 2/2001 | Lutz |
| 6,214,006 B1 | 4/2001 | Metz-Stavenhagen |
| 6,217,331 B1 | 4/2001 | Rogers et al. |
| 6,224,598 B1 | 5/2001 | Jackson |
| 6,248,105 B1 | 6/2001 | Schlaepfer et al. |
| 6,261,287 B1 | 7/2001 | Metz-Stavenhagen |
| 6,273,914 B1 | 8/2001 | Papas |
| 6,280,442 B1 | 8/2001 | Barker et al. |
| 6,296,642 B1 | 10/2001 | Morrison et al. |
| 6,325,802 B1 | 12/2001 | Frigg |

(56) References Cited

U.S. PATENT DOCUMENTS

| | | |
|---|---|---|
| 6,355,040 B1 | 3/2002 | Richelsoph et al. |
| 6,361,535 B2 | 3/2002 | Jackson |
| RE37,665 E | 4/2002 | Ralph et al. |
| 6,368,321 B1 | 4/2002 | Jackson |
| 6,402,752 B2 | 6/2002 | Schaeffler-Wachter et al. |
| 6,440,132 B1 | 8/2002 | Jackson |
| 6,443,953 B1 | 9/2002 | Perra et al. |
| 6,443,955 B1 | 9/2002 | Ahrend et al. |
| 6,451,021 B1 | 9/2002 | Ralph et al. |
| 6,454,768 B1 | 9/2002 | Jackson |
| 6,454,772 B1 | 9/2002 | Jackson |
| 6,471,705 B1 | 10/2002 | Biedermann et al. |
| 6,482,207 B1 | 11/2002 | Errico |
| 6,485,491 B1 | 11/2002 | Farris et al. |
| 6,491,696 B1 | 12/2002 | Kunkel |
| 6,508,820 B2 | 1/2003 | Bales |
| 6,514,255 B1 | 2/2003 | Ferree |
| 6,520,963 B1 | 2/2003 | McKinley |
| 6,533,226 B2 | 3/2003 | Geiger |
| 6,537,070 B1 | 3/2003 | Stucki-McCormick |
| 6,537,276 B2 | 3/2003 | Metz-Stavenhagen |
| 6,554,831 B1 | 4/2003 | Rivard et al. |
| 6,558,387 B2 | 5/2003 | Errico et al. |
| 6,565,565 B1 | 5/2003 | Yuan et al. |
| 6,585,740 B2 | 7/2003 | Schlapfer et al. |
| 6,616,667 B1 | 9/2003 | Steiger et al. |
| 6,626,908 B2 | 9/2003 | Cooper et al. |
| 6,641,586 B2 | 11/2003 | Varieur |
| 6,641,588 B2 | 11/2003 | Citron et al. |
| 6,660,004 B2 | 12/2003 | Barker et al. |
| 6,689,140 B2 | 2/2004 | Cohen |
| 6,695,852 B2 | 2/2004 | Gleason |
| 6,716,214 B1 | 4/2004 | Jackson |
| 6,726,687 B2 | 4/2004 | Jackson |
| 6,736,820 B2 | 5/2004 | Biedermann et al. |
| 6,738,527 B2 | 5/2004 | Kuwata et al. |
| 6,740,086 B2 | 5/2004 | Richelsoph |
| 6,749,613 B1 | 6/2004 | Conchy et al. |
| 6,755,829 B1 | 6/2004 | Bono et al. |
| 6,770,075 B2 | 8/2004 | Howland |
| 6,780,186 B2 | 8/2004 | Errico et al. |
| 6,783,527 B2 | 8/2004 | Drewry et al. |
| 6,802,844 B2 | 10/2004 | Ferree |
| 6,827,719 B2 | 12/2004 | Ralph et al. |
| 6,835,196 B2 | 12/2004 | Biedermann et al. |
| 6,840,940 B2 | 1/2005 | Ralph et al. |
| 6,843,791 B2 | 1/2005 | Serhan |
| 6,866,664 B2 | 3/2005 | Schaer et al. |
| 6,869,433 B2 | 3/2005 | Glascott |
| 6,887,275 B2 | 5/2005 | Carchidi et al. |
| 6,918,911 B2 | 7/2005 | Biedermann et al. |
| 6,933,440 B2 | 8/2005 | Ichikawa et al. |
| 6,964,666 B2 | 11/2005 | Jackson |
| 6,974,460 B2 | 12/2005 | Carbone et al. |
| 6,981,973 B2 | 1/2006 | McKinley |
| 7,008,227 B2 | 3/2006 | Carmichael et al. |
| 7,018,378 B2 | 3/2006 | Biedermann et al. |
| RE39,089 E | 5/2006 | Ralph et al. |
| 7,073,415 B2 | 7/2006 | Casutt et al. |
| 7,081,117 B2 | 7/2006 | Bono et al. |
| 7,087,057 B2 | 8/2006 | Konieczynski et al. |
| D527,678 S | 9/2006 | Warner |
| 7,125,410 B2 | 10/2006 | Freudiger |
| 7,125,426 B2 | 10/2006 | Moumene et al. |
| 7,128,743 B2 | 10/2006 | Metz-Stavenhagen |
| 7,131,467 B2 | 11/2006 | Gao et al. |
| 7,144,396 B2 | 12/2006 | Shluzas |
| 7,163,539 B2 | 1/2007 | Abdelgany et al. |
| 7,175,622 B2 | 2/2007 | Farris |
| 7,186,255 B2 | 3/2007 | Baynham et al. |
| 7,211,086 B2 | 5/2007 | Biedermann et al. |
| 7,223,268 B2 | 5/2007 | Biedermann |
| 7,250,052 B2 | 7/2007 | Landry et al. |
| 7,270,665 B2 | 9/2007 | Morrison et al. |
| 7,316,684 B1 | 1/2008 | Baccelli et al. |
| 7,322,548 B2 | 1/2008 | Mielke et al. |
| 7,330,490 B2 | 2/2008 | Furukawa et al. |
| 7,338,490 B2 | 3/2008 | Ogilvie et al. |
| 7,445,627 B2 | 11/2008 | Hawkes et al. |
| 7,452,360 B2 | 11/2008 | Trudeau et al. |
| 7,476,239 B2 | 1/2009 | Jackson |
| 7,547,319 B2 | 6/2009 | Segal et al. |
| 7,591,839 B2 | 9/2009 | Biedermann et al. |
| 7,592,546 B2 | 9/2009 | Johansson |
| 7,645,282 B2 | 1/2010 | Huxel et al. |
| 7,648,520 B2 | 1/2010 | Markworth |
| 7,691,131 B2 | 4/2010 | Graf |
| 7,708,762 B2 | 5/2010 | McCarthy et al. |
| 7,766,944 B2 | 8/2010 | Metz-Stavenhagen |
| 7,780,706 B2 | 8/2010 | Marino et al. |
| 7,785,352 B2 | 8/2010 | Snyder et al. |
| 7,785,354 B2 | 8/2010 | Biedermann et al. |
| 7,799,054 B2 | 9/2010 | Kwak et al. |
| 7,803,174 B2 | 9/2010 | Denis et al. |
| 7,806,895 B2 | 10/2010 | Weier et al. |
| 7,819,902 B2 | 10/2010 | Abdelgany et al. |
| 7,951,172 B2 | 5/2011 | Chao et al. |
| 7,967,849 B2 | 6/2011 | Carson et al. |
| 8,001,946 B2 | 8/2011 | Leitl |
| 8,002,806 B2 | 8/2011 | Justis |
| 8,029,513 B2 | 10/2011 | Konno et al. |
| 8,029,546 B2 | 10/2011 | Capote et al. |
| 8,038,701 B2 | 10/2011 | Rock et al. |
| 8,096,998 B2 | 1/2012 | Cresina |
| 8,100,946 B2 | 1/2012 | Strausbaugh et al. |
| 8,137,356 B2 | 3/2012 | Hestad et al. |
| 8,162,946 B2 | 4/2012 | Baccelli et al. |
| 8,162,986 B2 | 4/2012 | Zehnder |
| 8,172,772 B2 | 5/2012 | Zwolinski et al. |
| 8,197,517 B1 | 6/2012 | Lab et al. |
| 8,216,245 B2 | 7/2012 | Gil et al. |
| 8,221,464 B2 | 7/2012 | Belliard et al. |
| 8,231,626 B2 | 7/2012 | Hulliger et al. |
| 8,241,333 B2 | 8/2012 | Jackson |
| 8,246,659 B2 | 8/2012 | Vonwiller et al. |
| 8,257,367 B2 | 9/2012 | Bryant et al. |
| 8,308,782 B2 | 11/2012 | Jackson |
| 8,317,836 B2 | 11/2012 | Zucherman et al. |
| 8,323,318 B2 | 12/2012 | Baccelli et al. |
| 8,444,681 B2 | 5/2013 | Jackson et al. |
| 8,469,960 B2 | 6/2013 | Hutton et al. |
| 8,469,966 B2 | 6/2013 | Allen et al. |
| 8,556,938 B2 | 10/2013 | Jackson et al. |
| 8,628,558 B2 | 1/2014 | Harvey et al. |
| 8,632,572 B2 | 1/2014 | Darst et al. |
| 8,663,298 B2 | 3/2014 | Keyer et al. |
| 8,758,411 B1 | 6/2014 | Rayon et al. |
| 8,814,910 B2 | 8/2014 | Baccelli et al. |
| 8,840,652 B2 | 9/2014 | Jackson |
| 8,870,869 B2 | 10/2014 | Meunier et al. |
| 8,870,870 B2 | 10/2014 | Baccelli et al. |
| 8,882,803 B2 | 11/2014 | Iott et al. |
| 8,911,470 B2 | 12/2014 | Mirza et al. |
| 8,911,478 B2 | 12/2014 | Jackson et al. |
| 8,911,479 B2 | 12/2014 | Jackson et al. |
| 8,926,672 B2 | 1/2015 | Jackson et al. |
| 8,979,904 B2 | 3/2015 | Jackson et al. |
| 8,998,959 B2 | 4/2015 | Jackson et al. |
| 8,998,961 B1 | 4/2015 | Ziemek et al. |
| 9,039,708 B2 | 5/2015 | Larroque-Lahitette |
| 9,168,069 B2 | 10/2015 | Jackson et al. |
| 9,216,041 B2 | 12/2015 | Jackson et al. |
| 9,320,546 B2 | 4/2016 | Keyer et al. |
| 9,326,796 B2 | 5/2016 | Harvey et al. |
| 9,393,047 B2 | 7/2016 | Jackson et al. |
| 9,439,681 B2 | 9/2016 | Keyer et al. |
| 9,451,993 B2 | 9/2016 | Jackson et al. |
| 9,480,517 B2 | 11/2016 | Jackson et al. |
| 9,504,496 B2 | 11/2016 | Jackson et al. |
| 9,522,021 B2 | 12/2016 | Jackson et al. |
| 9,636,146 B2 | 5/2017 | Jackson et al. |
| 9,717,533 B2 | 8/2017 | Jackson et al. |
| 9,717,534 B2 | 8/2017 | Jackson et al. |
| 10,105,163 B2 | 10/2018 | Keyer et al. |

(56) References Cited

U.S. PATENT DOCUMENTS

| | | | |
|---|---|---|---|
| 10,136,923 B2* | 11/2018 | Keyer | A61B 17/7037 |
| 10,154,859 B2 | 12/2018 | Keyer et al. | |
| 2001/0047173 A1 | 11/2001 | Schlapfer et al. | |
| 2002/0045899 A1 | 4/2002 | Errico et al. | |
| 2002/0068940 A1 | 6/2002 | Gaines | |
| 2002/0069537 A1 | 6/2002 | Wenzler | |
| 2002/0072753 A1 | 6/2002 | Cohen | |
| 2002/0103487 A1 | 8/2002 | Errico et al. | |
| 2002/0117321 A1 | 8/2002 | Beebe et al. | |
| 2002/0120272 A1 | 8/2002 | Yuan et al. | |
| 2002/0138077 A1 | 9/2002 | Ferree | |
| 2002/0143341 A1 | 10/2002 | Biedermann et al. | |
| 2002/0151900 A1 | 10/2002 | Glascott | |
| 2003/0100896 A1 | 5/2003 | Biedermann et al. | |
| 2003/0100904 A1 | 5/2003 | Biedermann | |
| 2003/0125741 A1 | 7/2003 | Biedermann et al. | |
| 2003/0125742 A1 | 7/2003 | Yuan et al. | |
| 2003/0149431 A1 | 8/2003 | Varieur | |
| 2003/0153912 A1 | 8/2003 | Graf | |
| 2003/0163133 A1 | 8/2003 | Altarac et al. | |
| 2003/0176861 A1 | 9/2003 | Reed | |
| 2004/0006342 A1 | 1/2004 | Altarac et al. | |
| 2004/0024464 A1 | 2/2004 | Errico et al. | |
| 2004/0039384 A1 | 2/2004 | Boehm et al. | |
| 2004/0111088 A1 | 6/2004 | Picetti et al. | |
| 2004/0138660 A1 | 7/2004 | Serhan | |
| 2004/0143265 A1 | 7/2004 | Landry et al. | |
| 2004/0153077 A1 | 8/2004 | Biedermann et al. | |
| 2004/0157186 A1 | 8/2004 | Abels et al. | |
| 2004/0162558 A1 | 8/2004 | Hegde et al. | |
| 2004/0172022 A1 | 9/2004 | Landry et al. | |
| 2004/0181224 A1 | 9/2004 | Biedermann et al. | |
| 2004/0186473 A1 | 9/2004 | Cournoyer et al. | |
| 2004/0186474 A1 | 9/2004 | Matthis et al. | |
| 2004/0193160 A1 | 9/2004 | Richelsoph | |
| 2004/0199169 A1 | 10/2004 | Koons et al. | |
| 2004/0225292 A1 | 11/2004 | Sasso et al. | |
| 2004/0230192 A1 | 11/2004 | Graf | |
| 2004/0236330 A1 | 11/2004 | Purcell et al. | |
| 2004/0249380 A1 | 12/2004 | Glascott | |
| 2004/0267264 A1 | 12/2004 | Konieczynski et al. | |
| 2005/0033298 A1 | 2/2005 | Hawkes et al. | |
| 2005/0049588 A1 | 3/2005 | Jackson | |
| 2005/0049589 A1 | 3/2005 | Jackson | |
| 2005/0055026 A1 | 3/2005 | Biedermann et al. | |
| 2005/0080415 A1 | 4/2005 | Keyer et al. | |
| 2005/0080420 A1 | 4/2005 | Farris et al. | |
| 2005/0143737 A1 | 6/2005 | Pafford et al. | |
| 2005/0154389 A1 | 7/2005 | Selover et al. | |
| 2005/0154391 A1 | 7/2005 | Doherty et al. | |
| 2005/0171537 A1 | 8/2005 | Mazel et al. | |
| 2005/0171542 A1 | 8/2005 | Biedermann et al. | |
| 2005/0177154 A1 | 8/2005 | Moumene et al. | |
| 2005/0177166 A1 | 8/2005 | Timm et al. | |
| 2005/0177179 A1 | 8/2005 | Baynham et al. | |
| 2005/0187548 A1 | 8/2005 | Butler et al. | |
| 2005/0192571 A1 | 9/2005 | Abdelgany | |
| 2005/0203515 A1 | 9/2005 | Doherty et al. | |
| 2005/0203516 A1 | 9/2005 | Biedermann et al. | |
| 2005/0209592 A1 | 9/2005 | Schlapfer et al. | |
| 2005/0216001 A1 | 9/2005 | David | |
| 2005/0216003 A1 | 9/2005 | Biedermann et al. | |
| 2005/0228378 A1 | 10/2005 | Kalfas et al. | |
| 2005/0228385 A1 | 10/2005 | Iott et al. | |
| 2005/0234421 A1 | 10/2005 | Mishima et al. | |
| 2005/0234451 A1 | 10/2005 | Markworth | |
| 2005/0261687 A1 | 11/2005 | Garamszegi et al. | |
| 2005/0277928 A1 | 12/2005 | Boschert | |
| 2005/0283157 A1 | 12/2005 | Coates et al. | |
| 2005/0288671 A1 | 12/2005 | Yuan et al. | |
| 2006/0004357 A1 | 1/2006 | Lee et al. | |
| 2006/0025767 A1 | 2/2006 | Khalili | |
| 2006/0025770 A1 | 2/2006 | Schlapfer et al. | |
| 2006/0036252 A1 | 2/2006 | Baynham et al. | |
| 2006/0052818 A1 | 3/2006 | Drake et al. | |
| 2006/0064091 A1 | 3/2006 | Ludwig et al. | |
| 2006/0079892 A1 | 4/2006 | Roychowdhury et al. | |
| 2006/0084993 A1 | 4/2006 | Landry et al. | |
| 2006/0084995 A1 | 4/2006 | Biedermann et al. | |
| 2006/0084996 A1 | 4/2006 | Metz-Stavenhagen | |
| 2006/0089634 A1 | 4/2006 | Anderson et al. | |
| 2006/0089643 A1 | 4/2006 | Mujwid | |
| 2006/0100622 A1 | 5/2006 | Jackson | |
| 2006/0106383 A1 | 5/2006 | Biedermann et al. | |
| 2006/0111779 A1 | 5/2006 | Petersen | |
| 2006/0129149 A1 | 6/2006 | Iott et al. | |
| 2006/0142761 A1 | 6/2006 | Landry et al. | |
| 2006/0149232 A1 | 7/2006 | Sasing | |
| 2006/0149233 A1 | 7/2006 | Richelsoph | |
| 2006/0149241 A1 | 7/2006 | Richelsoph et al. | |
| 2006/0149265 A1 | 7/2006 | James et al. | |
| 2006/0155277 A1 | 7/2006 | Metz-Stavenhagen | |
| 2006/0173456 A1 | 8/2006 | Hawkes et al. | |
| 2006/0200131 A1 | 9/2006 | Chao et al. | |
| 2006/0212034 A1 | 9/2006 | Triplett et al. | |
| 2006/0217717 A1 | 9/2006 | Whipple | |
| 2006/0229611 A1 | 10/2006 | Avery et al. | |
| 2006/0235385 A1 | 10/2006 | Whipple | |
| 2006/0235393 A1 | 10/2006 | Bono et al. | |
| 2006/0241594 A1 | 10/2006 | McCarthy et al. | |
| 2006/0241599 A1 | 10/2006 | Konieczynski et al. | |
| 2006/0241624 A1 | 10/2006 | Kizuka et al. | |
| 2006/0247636 A1 | 11/2006 | Yuan et al. | |
| 2006/0247668 A1 | 11/2006 | Park | |
| 2006/0271047 A1 | 11/2006 | Jackson | |
| 2006/0282080 A1 | 12/2006 | Todd et al. | |
| 2006/0293659 A1 | 12/2006 | Alvarez | |
| 2006/0293664 A1 | 12/2006 | Schumacher | |
| 2007/0016200 A1 | 1/2007 | Jackson | |
| 2007/0043365 A1 | 2/2007 | Ritland | |
| 2007/0049932 A1 | 3/2007 | Richelsoph et al. | |
| 2007/0055240 A1 | 3/2007 | Matthis et al. | |
| 2007/0088357 A1 | 4/2007 | Johnson et al. | |
| 2007/0090238 A1 | 4/2007 | Justis | |
| 2007/0118118 A1 | 5/2007 | Kwak et al. | |
| 2007/0118121 A1 | 5/2007 | Purcell et al. | |
| 2007/0118123 A1 | 5/2007 | Strausbaugh et al. | |
| 2007/0123860 A1 | 5/2007 | Francis et al. | |
| 2007/0123870 A1 | 5/2007 | Jeon et al. | |
| 2007/0135817 A1 | 6/2007 | Ensign | |
| 2007/0161987 A1 | 7/2007 | Capote et al. | |
| 2007/0161994 A1 | 7/2007 | Lowery et al. | |
| 2007/0167946 A1 | 7/2007 | Triplett et al. | |
| 2007/0167949 A1 | 7/2007 | Altarac et al. | |
| 2007/0179501 A1 | 8/2007 | Firkins | |
| 2007/0191844 A1 | 8/2007 | Carls et al. | |
| 2007/0198014 A1 | 8/2007 | Graf et al. | |
| 2007/0225711 A1 | 9/2007 | Ensign | |
| 2007/0233087 A1 | 10/2007 | Schlapfer | |
| 2007/0233091 A1 | 10/2007 | Naifeh et al. | |
| 2007/0246614 A1 | 10/2007 | Allmann et al. | |
| 2007/0250061 A1 | 10/2007 | Chin et al. | |
| 2007/0250064 A1 | 10/2007 | Darois et al. | |
| 2007/0270805 A1 | 11/2007 | Miller et al. | |
| 2007/0270817 A1 | 11/2007 | Rezach | |
| 2007/0270820 A1 | 11/2007 | Dickinson et al. | |
| 2007/0270880 A1 | 11/2007 | Lindemann et al. | |
| 2007/0282339 A1 | 12/2007 | Schwab | |
| 2007/0288004 A1 | 12/2007 | Alvarez | |
| 2008/0021455 A1 | 1/2008 | Chao et al. | |
| 2008/0021456 A1 | 1/2008 | Gupta et al. | |
| 2008/0039843 A1 | 2/2008 | Abdou | |
| 2008/0058805 A1 | 3/2008 | Stuart | |
| 2008/0058812 A1 | 3/2008 | Zehnder | |
| 2008/0086126 A1 | 4/2008 | Miller | |
| 2008/0103502 A1 | 5/2008 | Capote et al. | |
| 2008/0140075 A1 | 6/2008 | Ensign et al. | |
| 2008/0140135 A1 | 6/2008 | Konieczynski et al. | |
| 2008/0154277 A1 | 6/2008 | Machalk et al. | |
| 2008/0154308 A1 | 6/2008 | Sherman et al. | |
| 2008/0177260 A1 | 7/2008 | McKinley et al. | |
| 2008/0177323 A1 | 7/2008 | Null et al. | |
| 2008/0188260 A1 | 8/2008 | Xiao et al. | |
| 2008/0208257 A1 | 8/2008 | Matthys | |

(56) References Cited

U.S. PATENT DOCUMENTS

| | | |
|---|---|---|
| 2008/0215095 A1 | 9/2008 | Biedermann et al. |
| 2008/0234743 A1 | 9/2008 | Marik |
| 2008/0243185 A1 | 10/2008 | Felix et al. |
| 2008/0249570 A1 | 10/2008 | Carson et al. |
| 2008/0262552 A1 | 10/2008 | Kim |
| 2008/0262553 A1 | 10/2008 | Hawkins et al. |
| 2008/0269810 A1 | 10/2008 | Zhang et al. |
| 2008/0294194 A1 | 11/2008 | Capote et al. |
| 2008/0294202 A1 | 11/2008 | Peterson et al. |
| 2008/0306553 A1 | 12/2008 | Zucherman et al. |
| 2008/0312692 A1 | 12/2008 | Brennan et al. |
| 2009/0088803 A1 | 4/2009 | Justis et al. |
| 2009/0093847 A1 | 4/2009 | Wilcox |
| 2009/0105770 A1 | 4/2009 | Berrevoets et al. |
| 2009/0149887 A1 | 6/2009 | Schlaepfer et al. |
| 2009/0187217 A1 | 7/2009 | Weiman et al. |
| 2009/0198280 A1 | 8/2009 | Spratt et al. |
| 2009/0259256 A1 | 10/2009 | Miller |
| 2009/0270916 A1 | 10/2009 | Ramsay et al. |
| 2010/0004694 A1 | 1/2010 | Little |
| 2010/0042165 A1 | 2/2010 | Aflatoon |
| 2010/0057125 A1 | 3/2010 | Viker |
| 2010/0087864 A1 | 4/2010 | Klein et al. |
| 2010/0094345 A1 | 4/2010 | Saidha et al. |
| 2010/0145394 A1 | 6/2010 | Harvey et al. |
| 2010/0168797 A1 | 7/2010 | Graf |
| 2010/0191286 A1 | 7/2010 | Butler |
| 2010/0198272 A1 | 8/2010 | Keyer et al. |
| 2010/0241172 A1 | 9/2010 | Biyani et al. |
| 2010/0249843 A1 | 9/2010 | Wegrzyn, III |
| 2010/0276051 A1 | 11/2010 | Kanehira |
| 2010/0292736 A1 | 11/2010 | Schwab |
| 2010/0298890 A1 | 11/2010 | Marino |
| 2010/0298891 A1 | 11/2010 | Jackson |
| 2010/0305621 A1 | 12/2010 | Wang et al. |
| 2010/0313428 A1 | 12/2010 | Mocanu |
| 2010/0318131 A1 | 12/2010 | James et al. |
| 2010/0324599 A1 | 12/2010 | Montello et al. |
| 2011/0087289 A1 | 4/2011 | Pham et al. |
| 2011/0106166 A1 | 5/2011 | Keyer et al. |
| 2011/0118791 A1 | 5/2011 | Nunley et al. |
| 2011/0213424 A1 | 9/2011 | Biedermann et al. |
| 2011/0230917 A1 | 9/2011 | Carson et al. |
| 2011/0270325 A1 | 11/2011 | Keyer et al. |
| 2011/0276051 A1 | 11/2011 | Blakemore et al. |
| 2012/0010629 A1 | 1/2012 | Mire et al. |
| 2012/0089194 A1 | 4/2012 | Strausbaugh et al. |
| 2012/0101533 A1 | 4/2012 | Purcell et al. |
| 2012/0109200 A1 | 5/2012 | Cahill et al. |
| 2012/0265249 A1 | 10/2012 | Fielding et al. |
| 2013/0012955 A1 | 1/2013 | Lin |
| 2013/0012995 A1 | 1/2013 | Butterfield et al. |
| 2013/0018421 A1 | 1/2013 | George et al. |
| 2013/0079827 A1 | 3/2013 | Neary et al. |
| 2013/0261680 A1 | 10/2013 | Baccelli et al. |
| 2013/0268011 A1 | 10/2013 | Rezach et al. |
| 2018/0036041 A1 | 2/2018 | Pham et al. |

FOREIGN PATENT DOCUMENTS

| | | |
|---|---|---|
| CN | 1997321 A | 7/2007 |
| CN | 102368967 A | 3/2012 |
| CN | 102458279 A | 5/2012 |
| DE | 9314297 U1 | 4/1994 |
| DE | 4329220 A1 | 3/1995 |
| DE | 29903342 U1 | 6/1999 |
| DE | 29810798 U1 | 10/1999 |
| DE | 19912364 A1 | 10/2000 |
| DE | 20207785 U1 | 9/2003 |
| EP | 0408489 B1 | 9/1994 |
| EP | 0674880 A1 | 10/1995 |
| EP | 0828459 A1 | 3/1998 |
| EP | 0837656 A1 | 4/1998 |
| EP | 0612507 B1 | 12/1998 |
| EP | 0683644 B1 | 6/2000 |
| EP | 1198205 A1 | 4/2002 |
| EP | 1210914 A1 | 6/2002 |
| EP | 0807420 B1 | 7/2002 |
| EP | 1248573 A1 | 10/2002 |
| EP | 1269929 A1 | 1/2003 |
| EP | 1316295 A2 | 6/2003 |
| EP | 1323391 A2 | 7/2003 |
| EP | 1637085 A2 | 3/2006 |
| EP | 1313403 B1 | 10/2006 |
| EP | 1741396 A1 | 1/2007 |
| EP | 1815812 A1 | 8/2007 |
| EP | 1665994 B1 | 6/2008 |
| EP | 1928358 A2 | 6/2008 |
| EP | 1961392 A1 | 8/2008 |
| EP | 2052690 A1 | 4/2009 |
| EP | 1294297 B1 | 8/2010 |
| ES | 2330132 T3 | 12/2009 |
| GB | 0820252 | 9/1959 |
| GB | 2414674 B | 8/2009 |
| GB | 2465156 A | 5/2010 |
| JP | 06-154258 | 6/1994 |
| JP | 08-112291 A | 5/1996 |
| JP | 08-206976 A | 8/1996 |
| JP | 2005-510286 | 4/2005 |
| JP | 2006-508748 A | 3/2006 |
| JP | 2006-154258 | 6/2006 |
| JP | 2006-525102 A | 11/2006 |
| JP | 2009-535114 A | 10/2009 |
| JP | 2012-523927 A | 10/2012 |
| JP | 2012-530550 A | 12/2012 |
| KR | 10-2008-0112851 A | 12/2008 |
| KR | 10-0896043 B1 | 5/2009 |
| KR | 10-2012-0013312 A | 2/2012 |
| KR | 10-2012-0039622 A | 4/2012 |
| WO | 94/17736 A1 | 8/1994 |
| WO | 96/32071 A1 | 10/1996 |
| WO | 97/02786 A1 | 1/1997 |
| WO | 98/08454 | 3/1998 |
| WO | 98/52482 A1 | 11/1998 |
| WO | 2000/015125 A1 | 3/2000 |
| WO | 00/21455 A1 | 4/2000 |
| WO | 01/06940 A1 | 2/2001 |
| WO | 01/52758 A1 | 7/2001 |
| WO | 02/00124 A1 | 1/2002 |
| WO | 02/17803 A2 | 3/2002 |
| WO | 02/76314 A1 | 10/2002 |
| WO | 2003/045261 A1 | 6/2003 |
| WO | 2004/052218 A1 | 6/2004 |
| WO | 2004/089245 A2 | 10/2004 |
| WO | 2004/098425 A2 | 11/2004 |
| WO | 2005/016161 A1 | 2/2005 |
| WO | WO 2005/016161 | * 2/2005 | ............ A61B 17/70 |
| WO | 2006/088452 A2 | 8/2006 |
| WO | 2006/114437 A1 | 11/2006 |
| WO | 2006/116437 A2 | 11/2006 |
| WO | 2006/135555 A2 | 12/2006 |
| WO | 2007/038350 A2 | 4/2007 |
| WO | 2007/040824 A2 | 4/2007 |
| WO | 2007/045892 A1 | 4/2007 |
| WO | 2007/047711 A2 | 4/2007 |
| WO | 2007/127632 A2 | 11/2007 |
| WO | 2007/146032 A2 | 12/2007 |
| WO | 2008/027940 A1 | 3/2008 |
| WO | 2008/048953 A2 | 4/2008 |
| WO | 2008/069420 A1 | 6/2008 |
| WO | 2008/089096 A2 | 7/2008 |
| WO | 2008/146185 A1 | 12/2008 |
| WO | 2008/147663 A1 | 12/2008 |
| WO | 2009/001978 A1 | 12/2008 |
| WO | 2009/015100 A2 | 1/2009 |
| WO | 2010/030906 A1 | 3/2010 |
| WO | 2010/028287 A3 | 6/2010 |
| WO | 2010/120989 A1 | 10/2010 |

(56) References Cited

FOREIGN PATENT DOCUMENTS

| WO | 2010/148231 A1 | 12/2010 |
|---|---|---|
| WO | 2012/154772 A2 | 11/2012 |

OTHER PUBLICATIONS

U.S. Provisional Application Filed on Apr. 15, 2009 by Nicholas Theodore et. al., entitled "Revision Connector for Spinal Constructs", U.S. Appl. No. 61/169,336.
International Preliminary Report on Patentability dated May 3, 2011 in PCT application PCT/US2009/063056.
International Preliminary Report on Patentability dated Dec. 4, 2011 in application PCT/US2009/058788, 7 pgs.
International Patent Application No. PCT/US2010/039037: International Search Report dated Jan. 9, 2010, 5 pages.
International Patent Application No. PCT/US2010/039037: International Preliminary Report on Patentability dated Jul. 11, 2011, 14 pages.
International Patent Application No. PCT/US2009/056692: International Search Report and Written Opinion dated Dec. 3, 2009, 14 pages.
International Patent Application No. PCT/US2008/070670; International Preliminary Report on Patentability, dated Jul. 9, 2009, 6 pages.
International Patent Application No. PCT/US2008/070670: International Search Report dated Feb. 17, 2009, 3 pages.
International Patent Application No. PCT/US2010/031178: Notification of Transmittal of the International Preliminary Report on Patentability dated Jun. 14, 2011, 12 pages.
International Patent Application No. PCT/US2010/031178: International Search Report dated Jun. 22, 2010, 8 pages.
International Patent Application No. PCT/US2006/047986: International Search Report dated May 2, 2007, 2 pages.
International Patent Application No. PCT/US2006/037120: International Search Report dated Jul. 11, 2007, 4 pages.
Aebi et al., "AO ASIF Principles in Spine Surgery", Springer, 1998, 186-190.

\* cited by examiner

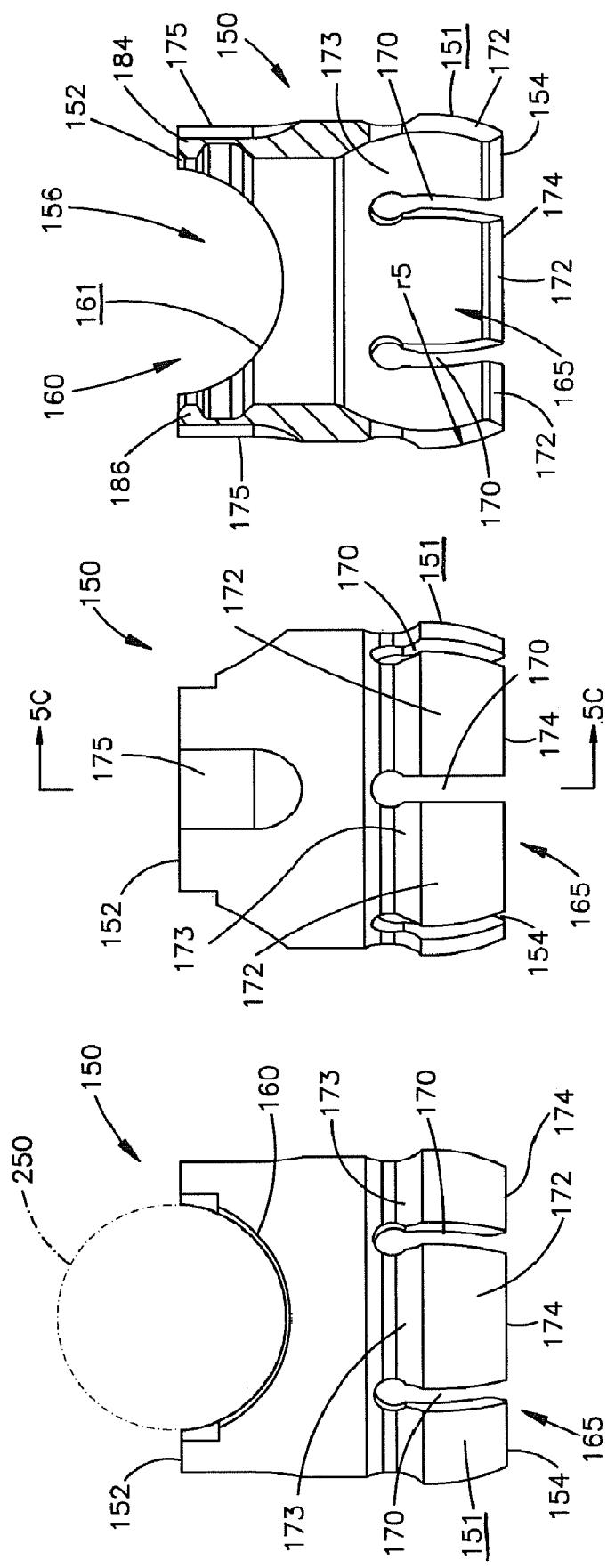

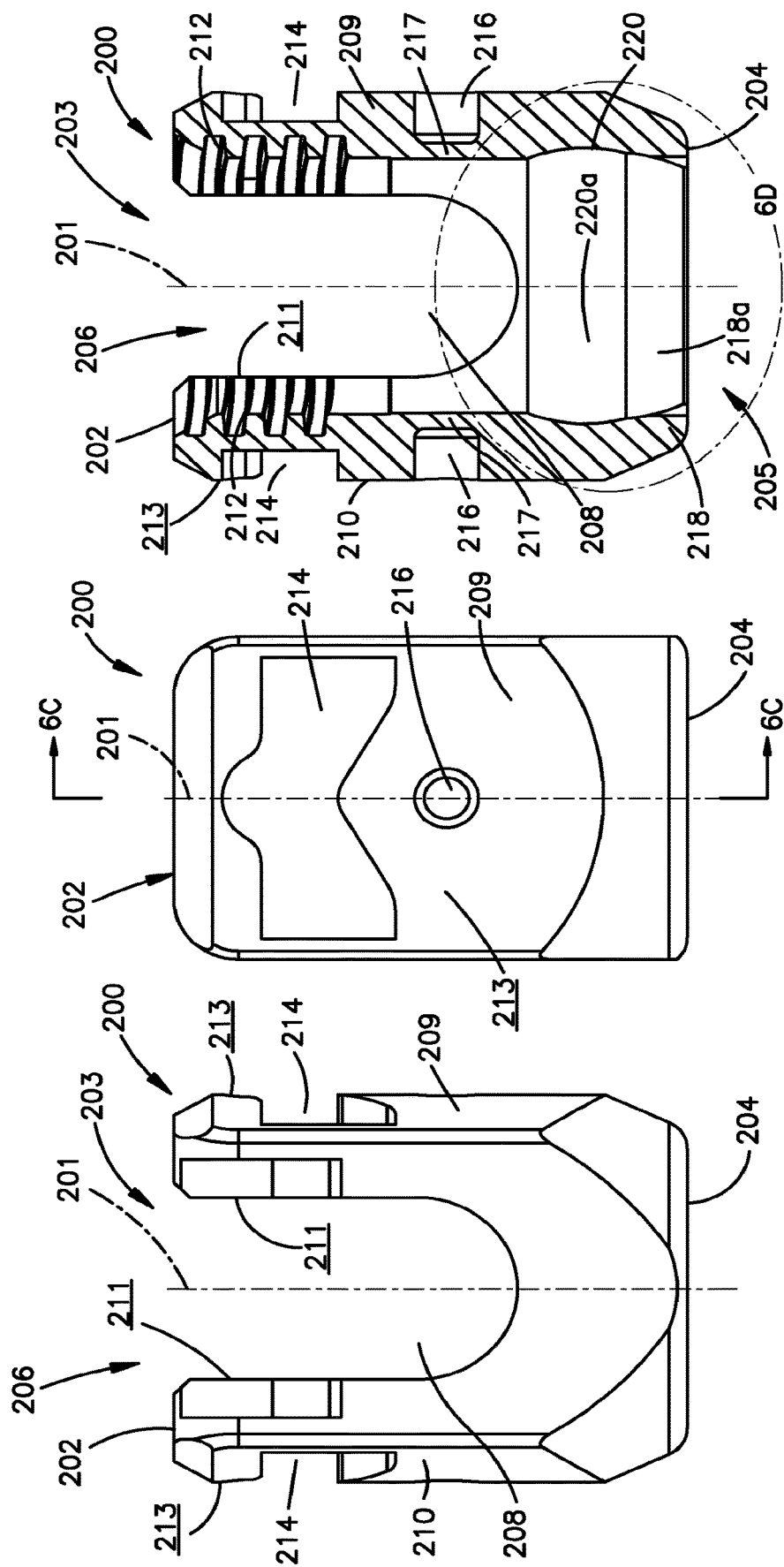

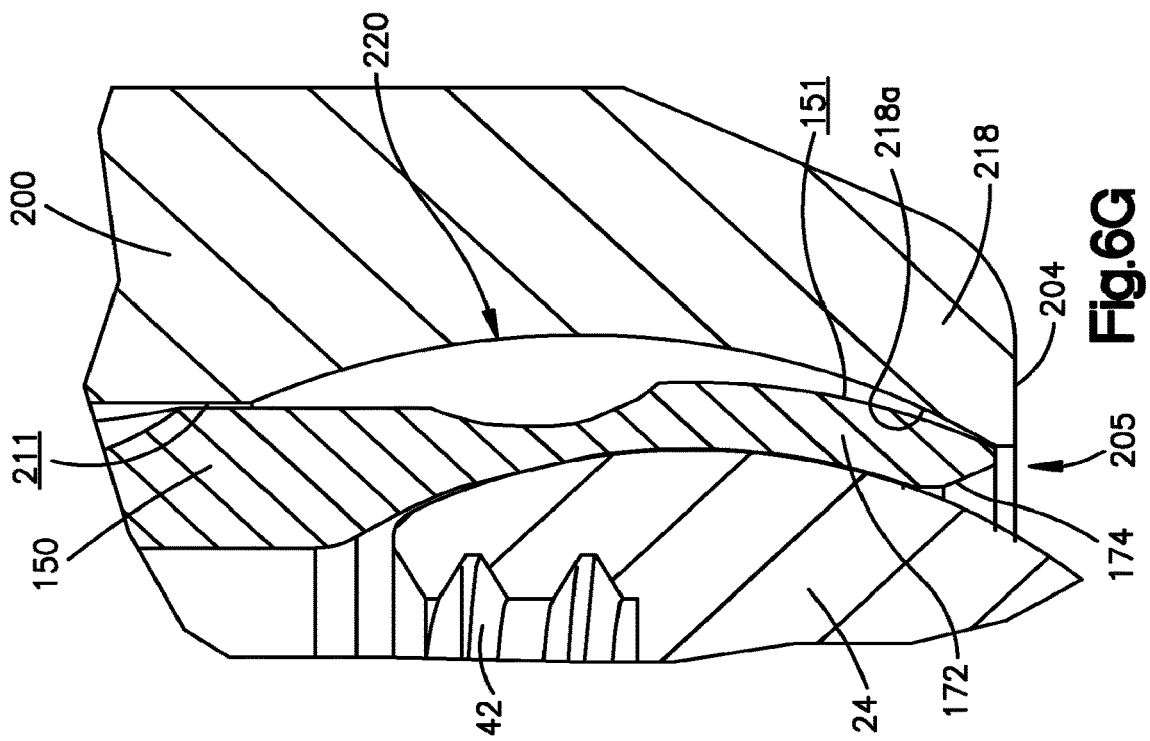
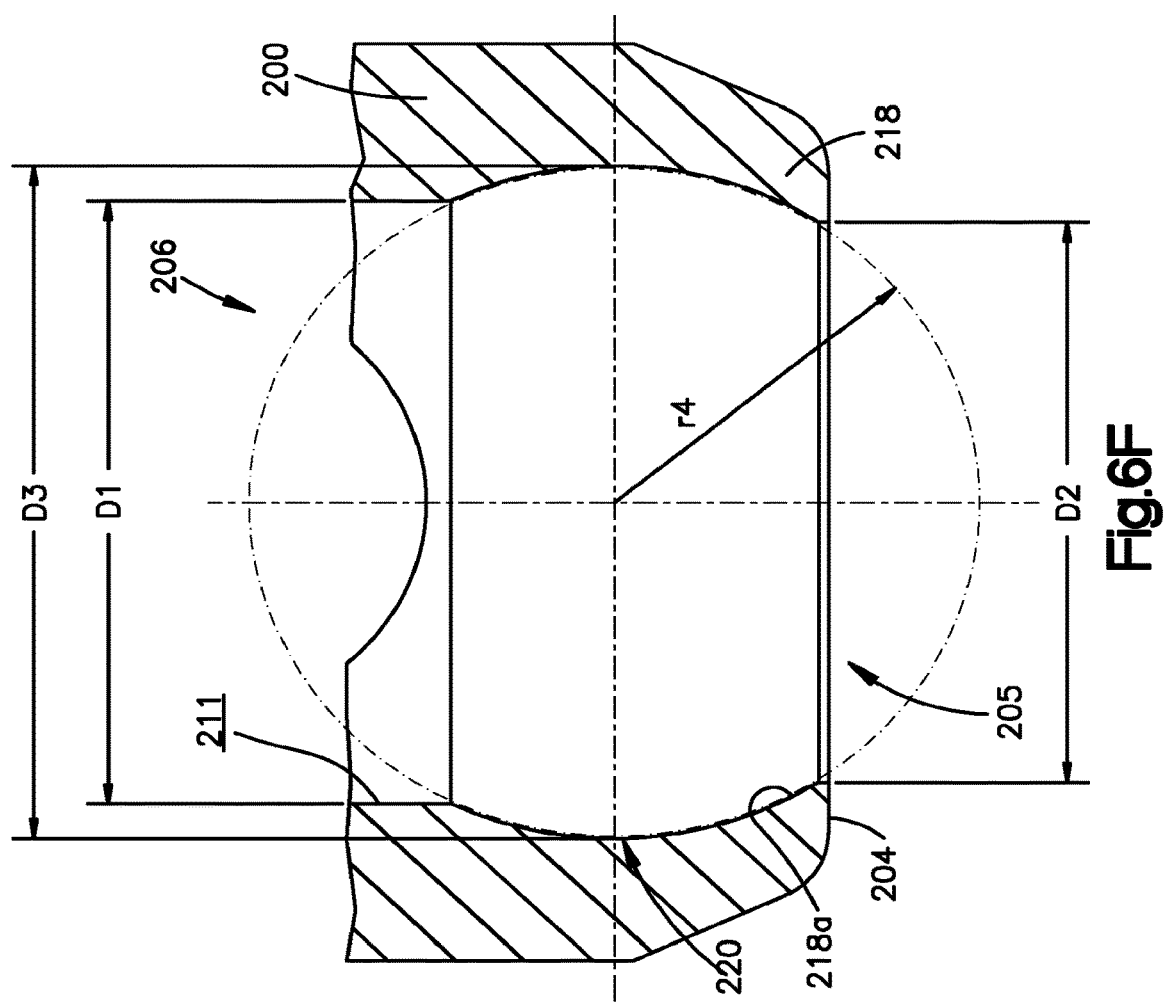
Fig.6F
Fig.6G

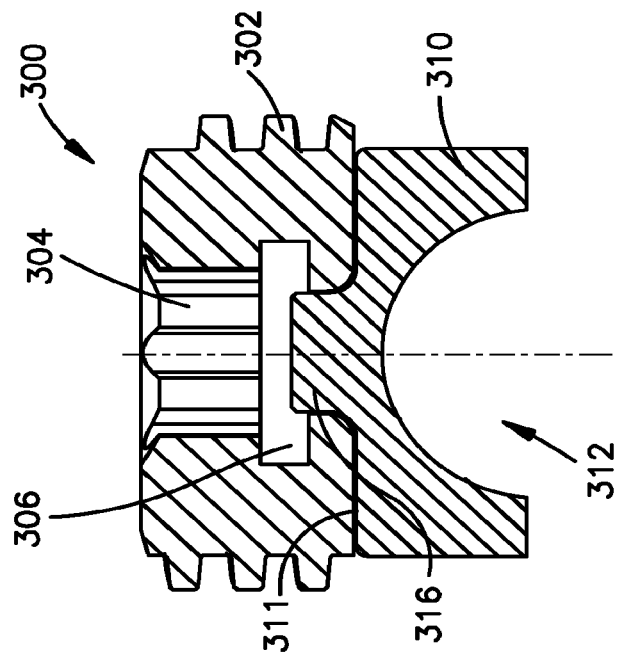
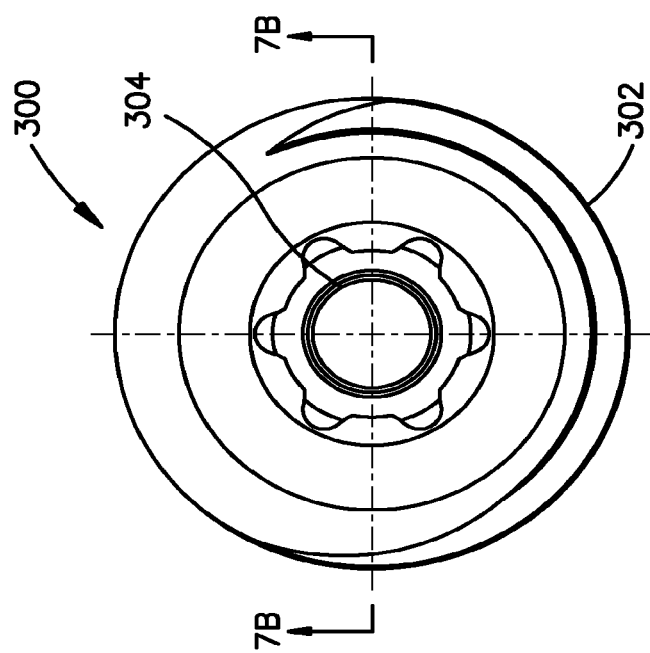

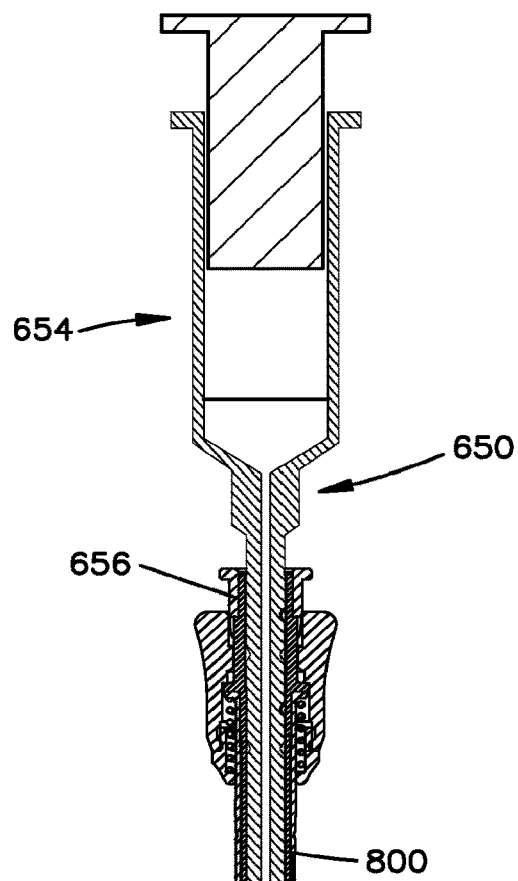
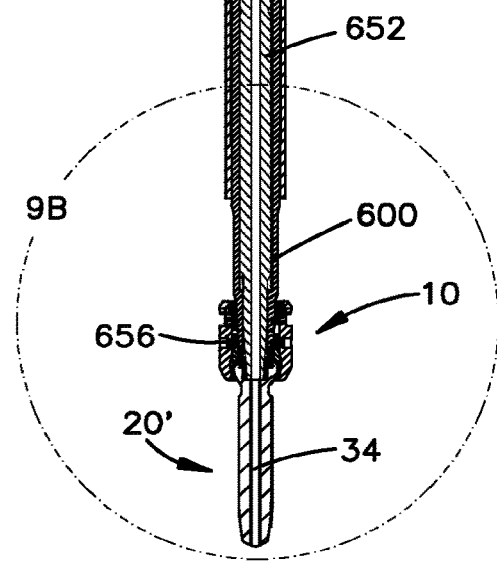
Fig.9A

POLYAXIAL BONE FIXATION ELEMENT

CROSS REFERENCE TO RELATED APPLICATIONS

This application is a continuation of U.S. application Ser. No. 15/254,382 filed Sep. 1, 2016, which is a continuation of U.S. application Ser. No. 14/163,482 filed Jan. 24, 2014, which is a continuation of U.S. application Ser. No. 12/669,224 filed Jan. 15, 2010, now U.S. Pat. No. 8,663,298 issued Mar. 4, 2014, which is a national phase under 35 U.S.C. § 371 of PCT Application No. PCT/US2008/070670 filed Jul. 21, 2008, which claims the benefit of U.S. Provisional Application No. 60/950,995 filed Jul. 20, 2007, and U.S. Provisional Application No. 60/988,584 filed Nov. 16, 2007, the entire contents of which are incorporated herein by reference in their entireties.

BACKGROUND

It is often necessary due to various spinal disorders to surgically correct and stabilize spinal curvatures, or to facilitate spinal fusion. Numerous systems for treating spinal disorders have been disclosed.

One method involves a pair of elongated members, typically spinal rods, longitudinally placed on the posterior spine on either side of spinous processes of the vertebral column. Each rod is attached to various vertebrae along the length of the spine by way of pedicle screws. The pedicle screws each may include a body having a U-shaped rod-receiving channel for receiving a portion of the longitudinal spinal rod therein. Moreover, the body often interacts with a locking cap to clamp and secure the position of the spinal rod within the rod-receiving channel.

To facilitate insertion of the spinal rod into the rod-receiving channels and to provide additional flexibility in the positioning of the spinal rods and the pedicle screws, pedicle screws have been developed wherein the body is pivotable with respect to the bone anchor (commonly known as polyaxial pedicle screws).

It is desirable to develop a pedicle screw that is simple for a surgeon to use, provides for polyaxial rotation and is able to securely mount the rod to the selected vertebra.

SUMMARY

A preferred embodiment of the present invention is directed to a polyaxial bone fixation element for use in a spinal fixation procedure. The polyaxial bone fixation element preferably includes a bone anchor having an enlarged head portion (e.g., a bone screw), a collet (e.g., an insert member), a body having an axial bore for receiving the collet and the enlarged head portion of the bone anchor. The body also includes a rod-receiving channel and threads for threadably receiving a locking cap (e.g., an externally threaded set screw). The polyaxial bone fixation element preferably enables in-situ assembly. That is, the polyaxial bone fixation element is preferably configured so that in use, the bone anchor may be secured to the patient's vertebra prior to being received within the body. Accordingly, the polyaxial bone fixation element preferably enables a surgeon to implant the bone anchor without the body and collet to maximize visibility and access around the anchoring site. Once the bone anchor has been secured to the patient's vertebra, the body can "pop-on" to the bone anchor. The bone anchor may also include an instrument interface so that a surgical instrument can be directly coupled to the bone anchor.

In one preferred embodiment, the polyaxial bone fixation element includes a bone anchor, a body, a collet and a locking cap. The bone anchor preferably includes an enlarged head portion. The head portion preferably includes a drive surface for engaging a first surgical instrument and an instrument interface for engaging a second surgical instrument. The body preferably includes a longitudinal axis, an upper end with an upper opening, a lower end with a lower opening, a bore extending between the upper opening and the lower opening wherein the bore has a first diameter, and a rod-receiving channel for receiving the spinal rod. The rod-receiving channel has a channel axis that is oriented substantially perpendicular to the longitudinal axis. The body preferably also includes a lower edge portion adjacent the lower opening. The lower edge portion has a second diameter smaller than the first diameter. The collet preferably includes a first end, a second end and one or more slots extending from the second end, wherein the slots define a plurality of flexible arms. The collet is preferably movably positioned within the bore of the body. The locking cap is preferably removably engageable with the body. The locking cap is movable from an unlocked position to a locked position, wherein movement of the locking cap from the unlocked position to the locked position urges the rod against the collet and the flexible arms against the lower edge portion to secure a position of the bone anchor relative to the body.

In another preferred embodiment, the polyaxial bone fixation element includes a body sized and configured to snap onto a head portion of an implanted bone anchor. The body preferably includes a longitudinal axis, an upper end with an upper opening, a lower end with a lower opening, a bore extending between the upper and lower openings wherein the bore has a first diameter, and a rod-receiving channel extending from the upper end toward the lower end and positioned on a channel axis that is oriented substantially perpendicular to the longitudinal axis. The bore preferably includes a lower edge portion terminating proximate the lower end and an enlarged diameter portion disposed adjacent to the lower edge portion and between the lower edge portion and the upper end. The lower edge portion preferably has a second diameter while the enlarged diameter portion has a third diameter, wherein the third diameter is preferably larger than the first diameter, which is larger than the second diameter. The collet preferably includes a first end, a second end and one or more slots extending from the second end, wherein the slots define a plurality of flexible arms. The flexible arms preferably each have a root end, a terminal end and a generally spherical, external surface proximate the terminal end. The flexible arms render the collet expandable to accept the head of the bone anchor and compressible to secure the head of the bone anchor relative to the collet. The flexible arms are preferably positioned proximate the enlarged diameter portion in a loading position and at least a portion of the external surface of the flexible arms contact the lower edge portion in a locked position.

In an alternate preferred embodiment, the polyaxial bone fixation element preferably includes a bone anchor, a body and a collet. The bone anchor preferably includes a head portion, wherein the head portion includes a drive surface for engaging a first surgical instrument and an instrument interface for engaging a second surgical instrument. The body preferably includes a longitudinal axis, an upper end with an upper opening, a lower end with a lower opening, a bore extending between the upper and lower openings, and a rod-receiving channel extending from the upper end toward the lower end and positioned on a channel axis that is oriented substantially perpendicular to the longitudinal axis. The bore preferably also includes a lower edge portion proximate the lower end and an enlarged diameter portion adjacent to the lower edge portion and between the lower edge portion and the upper end. The collet is preferably movably positioned within the bore of the body. The collet preferably includes a first end, a second end and one or more slots extending from the second end, wherein the slots define a plurality of flexible arms. The flexible arms preferably render the collet expandable to accept the head of the bone anchor and compressible to secure the head of the bone anchor relative to the collet. The collet preferably further includes a cavity extending from the second end. The flexible arms of the collet are preferably positioned in general vertical alignment with the enlarged diameter portion in a loading position so that the head of the bone anchor can be received in the cavity formed in the collet. At least a portion of the flexible arms preferably contact the lower edge portion in a locked position so that the head of the bone anchor is secured with respect to the collet. In the locked position, the contact is generally a line contact between the collet and the body.

BRIEF DESCRIPTION OF THE DRAWINGS

The foregoing summary, as well as the following detailed description of a preferred embodiment of the application, will be better understood when read in conjunction with the appended drawings. The preferred embodiment of the polyaxial bone fixation element is shown in the drawings for the purposes of illustration. It should be understood, however, that the application is not limited to the precise arrangements and instrumentalities shown. In the drawings:

FIG. 5A illustrates a front elevational view of a collet used in connection with the polyaxial bone fixation element shown in FIG. 1;

FIG. 5B illustrates a side elevational view of the collet shown in FIG. 5A;

FIG. 5C illustrates a cross-sectional view of the collet shown in FIG. 5A, taken along line 5C-5C of FIG. 5B;

FIG. 6A illustrates a front elevational view of a first preferred embodiment of a body used in connection with the polyaxial bone fixation element shown in FIG. 1;

FIG. 6B illustrates a side elevational view of the body shown in FIG. 6A;

FIG. 6C illustrates a cross-sectional view of the body shown in FIG. 6A, taken along line 6C-6C of FIG. 6B;

FIG. 6F illustrates a magnified, cross-sectional view of a second preferred embodiment of a lower end of a body of the polyaxial bone fixation element shown in FIG. 1;

FIG. 6G illustrates a magnified, cross-sectional view of the lower end of the body shown in FIG. 6F;

FIG. 7A illustrates a top plan view of a locking cap used in connection with the polyaxial bone fixation element shown in FIG. 1;

FIG. 7B illustrates a cross-sectional view of the locking cap shown in FIG. 7A, taken along line 7B-7B of FIG. 7A;

FIG. 9A illustrates a cross-sectional view of a syringe assembly and the sleeve coupled to a portion of the polyaxial bone fixation element of FIG. 1.

DETAILED DESCRIPTION OF ILLUSTRATIVE EMBODIMENTS

Figure 1:
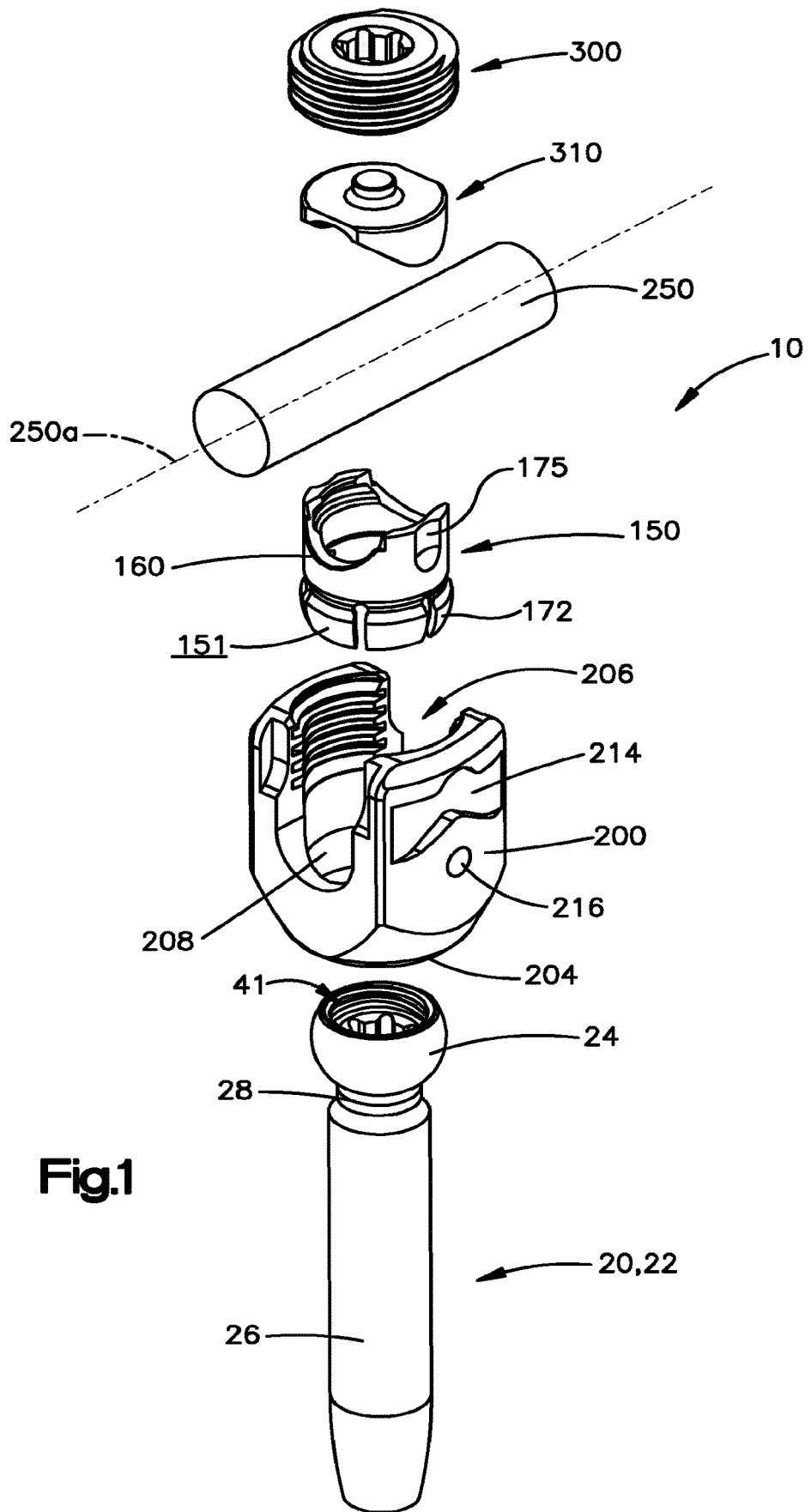
FIG. 1 illustrates an exploded, perspective view of a preferred embodiment of a polyaxial bone fixation element.
Figure 2:
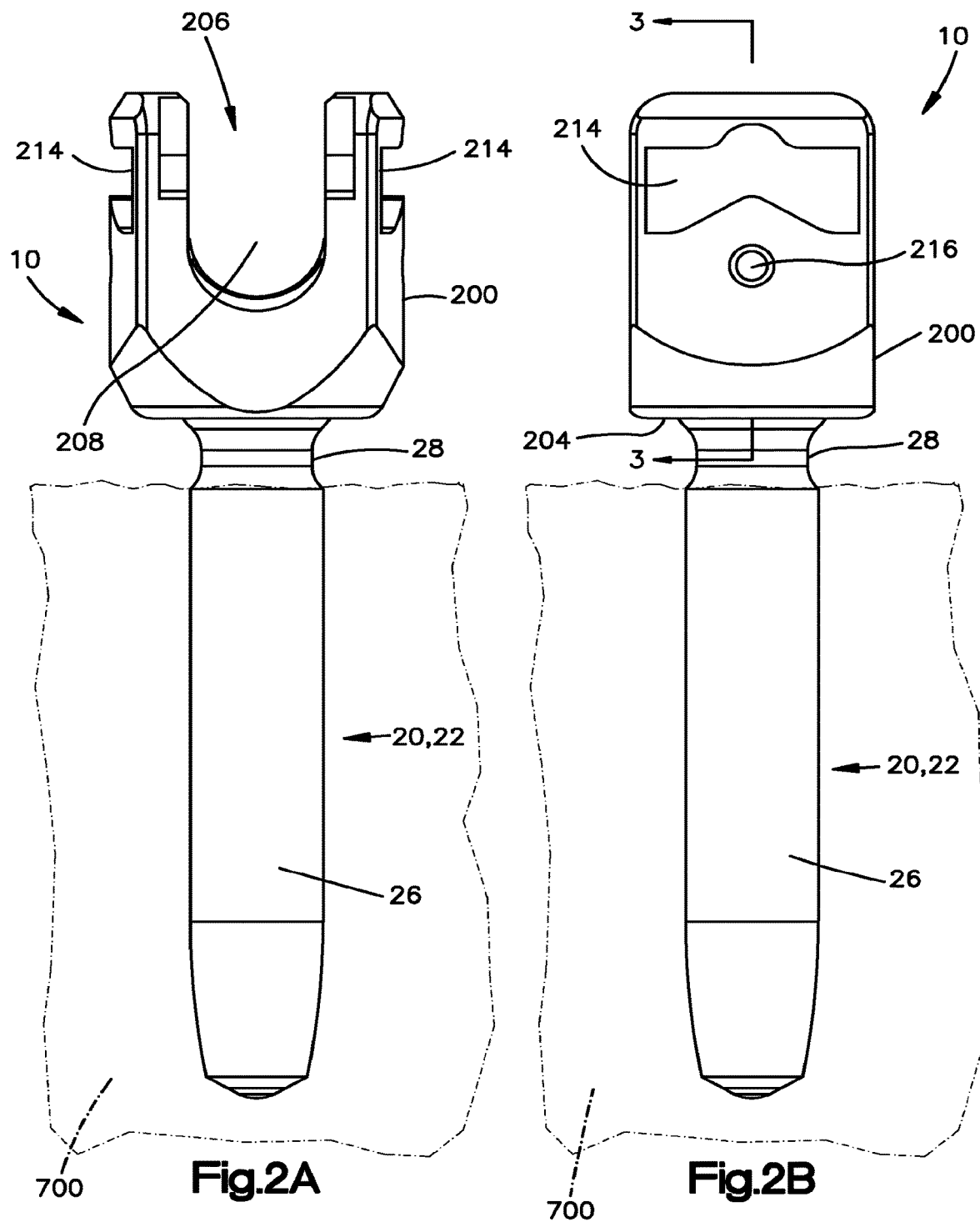
FIG. 2A illustrates a front elevational view of a portion the polyaxial bone fixation element shown in FIG. 1, mounted in a patient's vertebra.
FIG. 2B illustrates a side elevational view of the portion of the polyaxial bone fixation element shown in FIG. 1, mounted in the patient's vertebra.
Figure 3:
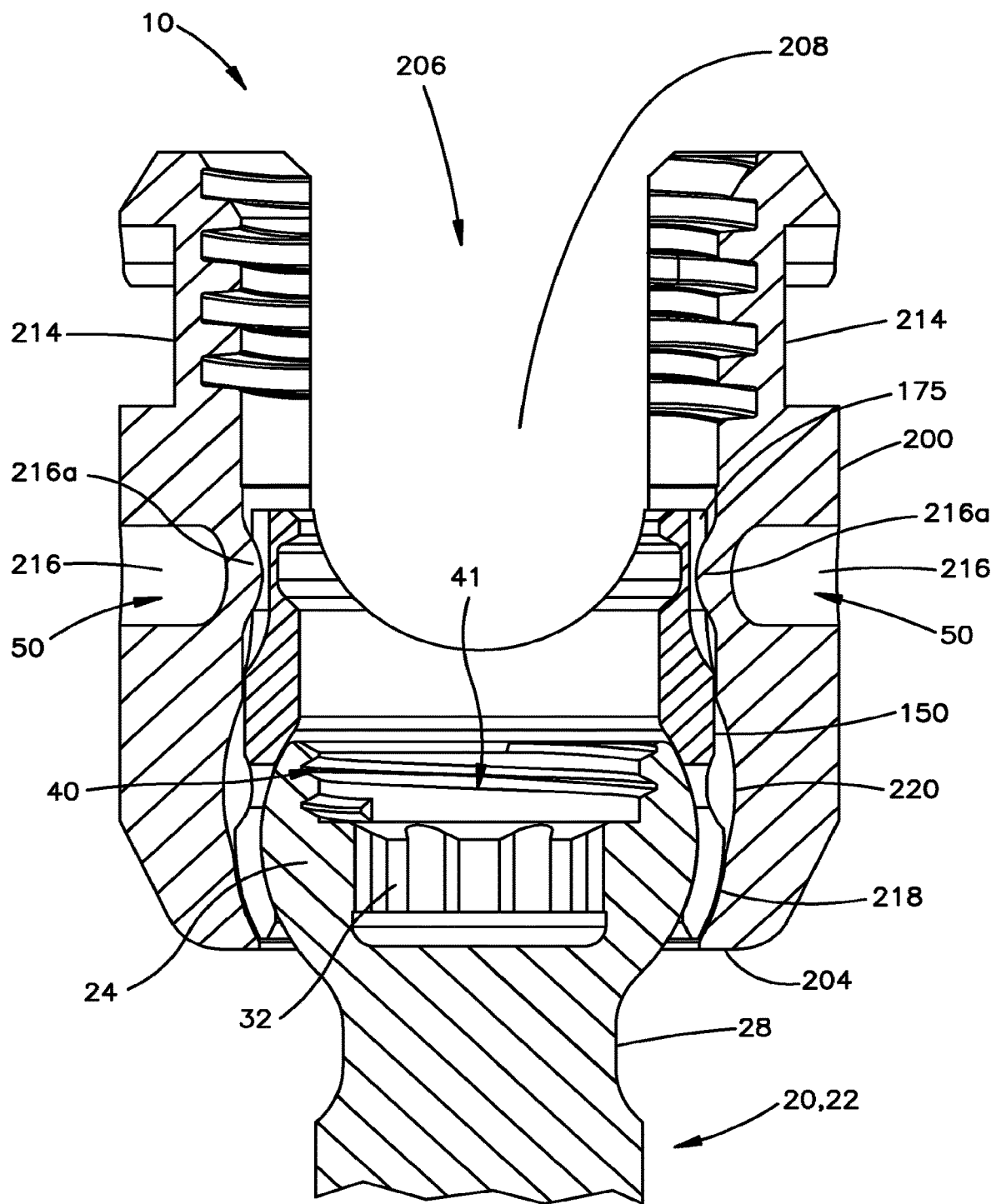
FIG. 3 illustrates a partial, cross-sectional view of the polyaxial bone fixation element shown in FIG. 1, taken along line 3-3 of FIG. 2B.
Figure 4A:
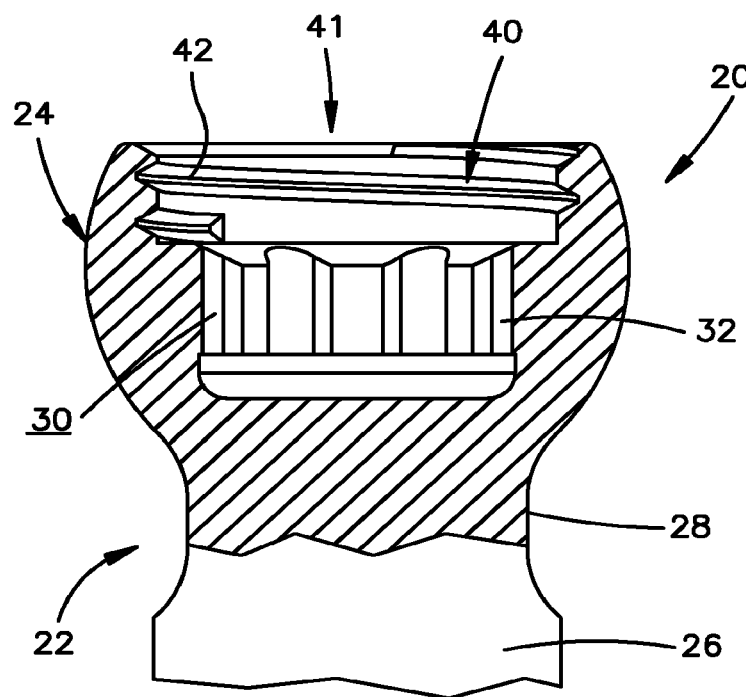
FIG. 4A illustrates a magnified cross-sectional view of a head portion of a bone anchor used in connection with the polyaxial bone fixation element shown in FIG. 1.
Figure 4B:
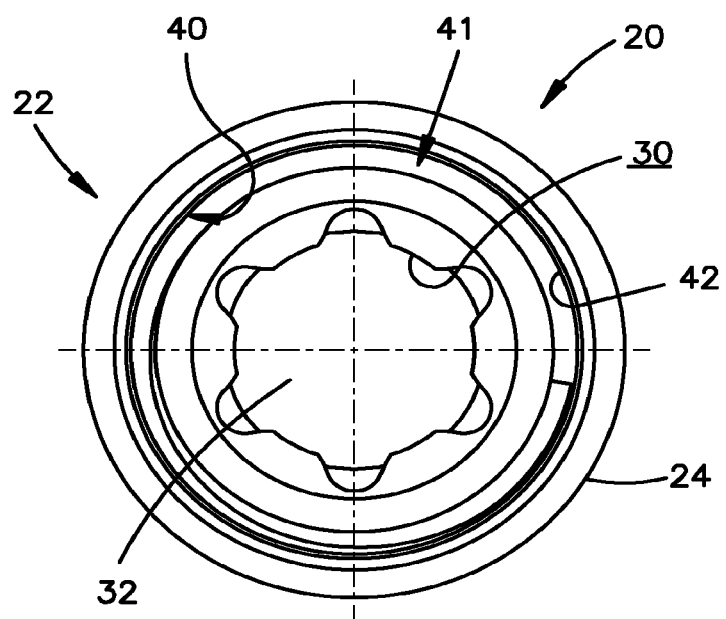
FIG. 4B illustrates a top plan view of the bone anchor shown in FIG. 4A.
Figure 6E:
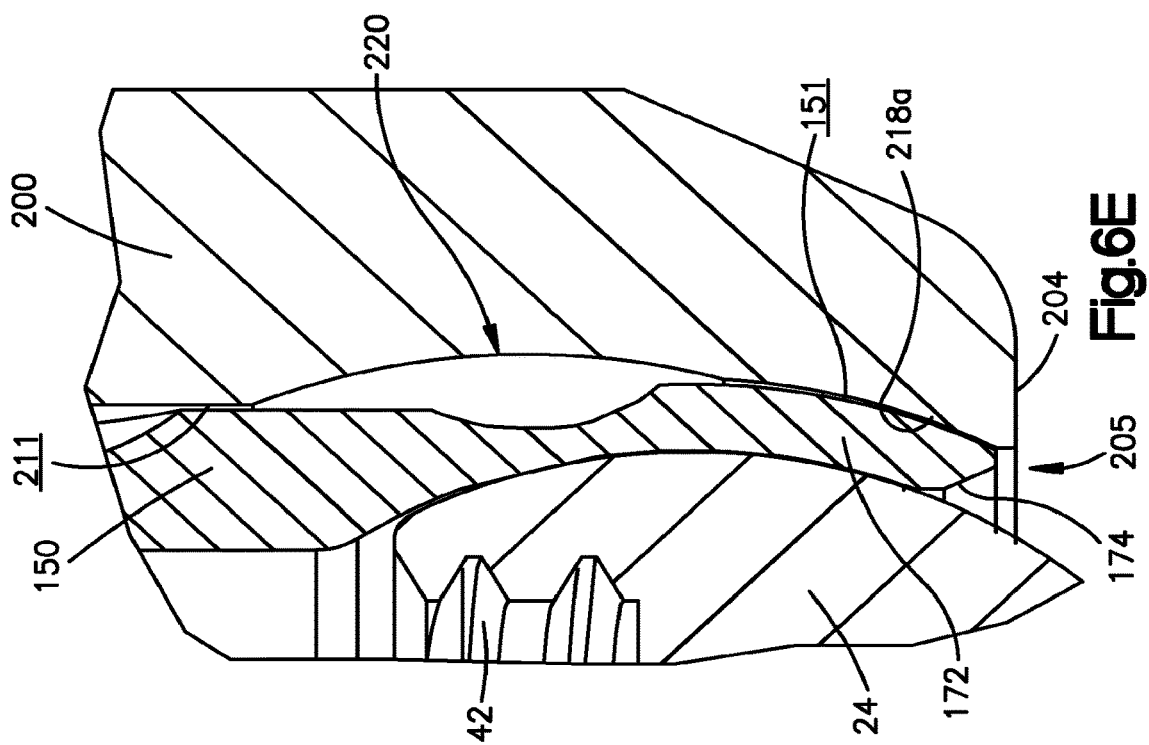
FIG. 6E illustrates a magnified, cross-sectional view of the lower end of the body shown in FIG. 6D and a collet and head of a bone anchor of the polyaxial bone fixation element shown in FIG. 1.
Figure 6D:
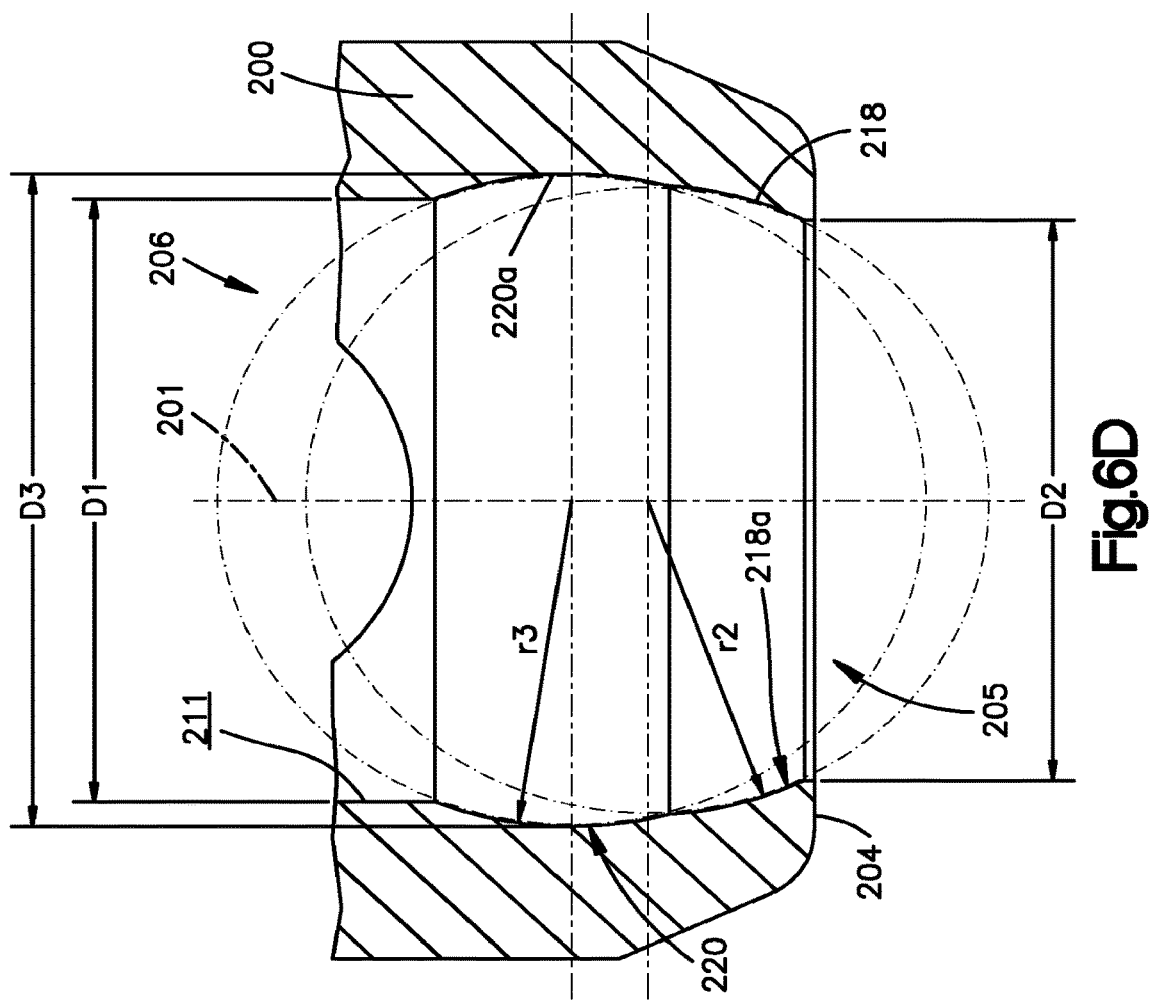
FIG. 6D illustrates a magnified, cross-sectional view of a lower end of the body shown in FIG. 6A, taken from within circle 6D of FIG. 6C.

Certain terminology is used in the following description for convenience only and is not limiting. The words "right", "left", "lower" and "upper" designate directions in the drawings to which reference is made. The words "inwardly" and "outwardly" refer to directions toward and away from, respectively, the geometric center of the polyaxial bone fixation element, the described instruments and designated parts thereof. The words, "anterior", "posterior", "superior", "inferior" and related words and/or phrases designate preferred positions and orientations in the human body to which reference is made and are not meant to be limiting. The terminology includes the above-listed words, derivatives thereof and words of similar import.

Certain exemplary embodiments of the invention will now be described with reference to the drawings. In general, such embodiments relate to a preferred polyaxial bone fixation element, and related instruments by way of non-limiting example and a polyaxial bone fixation element for use in spinal fixation to facilitate insertion of a longitudinal spinal rod in a rod-receiving channel formed in the body of the polyaxial bone fixation element. The invention may have other applications and uses and should not be limited to the structure or use described and illustrated.

Referring to FIGS. 1-7B, a preferred polyaxial bone fixation element 10 includes a bone anchor 20 (shown as a bone screw), a collet 150, a body 200, and a locking cap 300 (shown as an externally threaded set screw). As will be described in greater detail below, the polyaxial bone fixation element 10 preferably enables in-situ assembly. That is, preferably, the polyaxial bone fixation element 10 is configured so that in use, the bone anchor 20 may be secured to a patient's vertebra 700 prior to being received within the body 200. The polyaxial bone fixation element 10 preferably enables a surgeon to implant the bone anchor 20 without the body 200 and collet 150 pre-assembled to the bone anchor 20. By enabling the surgeon to implant the bone anchor 20 only, the polyaxial bone fixation element 10 maximizes visibility and access around the anchoring site. Once the bone anchor 20 has been secured to the patient's vertebra 700, the body 200 and collet 150 may "pop-on" to the bone anchor 20. Accordingly, the preferred polyaxial bone fixation element 10 is typically considered a bottom loading device, because the bone anchor 20 enters the body 200 through a lower or bottom end 204. Alternatively, the polyaxial bone fixation element 10 may be provided pre-assembled using identical components as described herein or may be configured for top loading with minor modifications, as would be apparent to one having ordinary skill in the art. Further, the collet 150 and body 200 assembly may be popped-off of the bone anchor 20 in-situ by arranging the collet 150 relative to the body 200 in a loading position, after the fixation element 10 has been arranged in the locked position, and removing the assembly from the bone anchor 20, as will be described in greater detail below.

While the polyaxial bone fixation element 10 will be described as and may generally be used in the spine (for example, in the lumbar, thoracic or cervical regions), those skilled in the art will appreciate that the polyaxial bone fixation element 10 may be used for fixation of other parts of the body such as, for example, joints, long bones or bones in the hand, face, feet, extremities, cranium, etc.

As will be described in greater detail below, several polyaxial bone fixation elements 10 may be used to secure a longitudinal spinal rod 250 to several vertebrae 700. It should be understood that the spinal rod 250 may include, but is not limited to, a solid rod, a non-solid rod, a flexible or dynamic rod, etc. It should be understood that the polyaxial bone fixation element 10 is not limited in use to any particular type of spinal rod 250.

Referring to FIGS. 1-4B, the bone anchor 20 preferably is in the form of a bone screw 22. Alternatively, however, the bone anchor 20 may be, for example, a hook or other fastener such as, a clamp, an implant, etc.

The bone screw 22 preferably includes an enlarged, curvate head portion 24 and an externally threaded shaft portion 26 for engaging the patient's vertebra 700. The specific features of the shaft 26 including, for example, thread pitch, shaft diameter, shaft shape, etc. are interchangeable, and it would be apparent to one having ordinary skill in the art that the bone screw 22 is not limited to any particular type of shaft 26. The bone screw 22 may or may not be cannulated (See FIGS. 9A and 9B). The bone screw 22 may also include a reduced diameter neck portion 28 between the head portion 24 and the shaft portion 26, which accommodates the polyaxial nature of the bone fixation element 10. The bone screw 22 may further be cannulated and fenestrated (not shown) such that openings extend outwardly from a central hollow channel in a cannulated screw to urge fluid out of the screw during injection or draw fluid into the central hollow channel from sides of the screw during extraction of material adjacent the screw.

Referring to FIGS. 3-4B and 8A-9B, the enlarged curvate head portion 24 preferably has a curvate or semi-spherical shape to facilitate rotation with respect to the collet 150, as will be described in greater detail below. The head portion 24 also preferably includes a drive surface 30 for receiving a corresponding tip 501 formed on a drive tool, such as a screw driver 500 (FIGS. 8A and 8B) for rotating the bone screw 22 into engagement with the patient's vertebra 700. The drive surface 30 may have any form now or hereafter known including, but not limited to, an external hexagon, a star drive pattern, a Phillips head pattern, a slot for a screw driver, a threading for a correspondingly threaded post, etc. Preferably, as shown, the drive surface 30 is comprised of a first tool interface or an internal recess 32, but is not so limited and may be comprised of an external drive feature that engages a female-type driver (not shown). The specific shape of the drive surface 30 or first tool interface 32 may be chosen to cooperate with the corresponding drive tool.

The head portion 24 may also include a second tool interface or a sleeve interface 40. The second tool interface 40 may be in any form now or hereafter known including, but not limited to, an internal or external thread, an external hexagon, a star drive pattern, a Phillips head pattern, a slot for a screw driver, a groove, a slot, etc. Preferably, however, the second tool interface 40 includes a plurality of threads 42 for threadably engaging a surgical instrument, such as a sleeve 600 (FIGS. 8A-9B), bone augmentation instrumentation, aspiration instrumentation, reduction tool for sagittal reduction or other reduction, coronal rotation tool, soft tissue refraction tool, kyphosis and lordosis correction tool, etc. The second tool interface 40 of the preferred embodiment permits application of forces to the bone anchor 20 along a longitudinal axis of the bone anchor 20, as well as along or at angles to the axis. In the preferred embodiment, the sleeve 600 is adaptable for use in combination with at least the screw driver 500 and an injection assembly 650. The surgical instrument may alternatively be any surgical instrument now or hereafter used in connection with a spinal fixation procedure including, but not limited to, a compressor, a distractor, minimally invasive instrumentation, etc. By incorporating the second tool interface 40 into the head portion 24 of the bone anchor 20, the sleeve 600 is able to directly engage the bone anchor 20 thus eliminating the need for the sleeve 600 to engage the body 200 of the polyaxial bone fixation element 10 and thereby, limiting toggling between the sleeve 600, screw driver 500 and/or bone anchor 20 in a working configuration, as will be described in greater detail below. In addition, the preferred second tool interface 40 permits application of forces to the bone anchor 20 through the sleeve 600 or another tool that mates with the second tool interface 40 to manipulate the bone anchor 20 and potentially the bone that the bone anchor 20 is mounted in.

Referring to FIGS. 3-4B, 8B and 9B, the second tool interface 40 and the first tool interface 32 are preferably formed in a head interface cavity 41 exposed from the top end of the head 24. Exposing both the second tool interface 40 and the first tool interface 32 at the top end of the head 24 permits simultaneous engagement of instruments with the second tool interface 40 and first tool interface 32 for manipulating the bone anchor 20. Both the second tool interface 40 and the first tool interface 32 may be engaged individually or simultaneously by an instrument prior to mounting the collet 150 and body 200 to the head 24 or after the collet 150 and body 200 are mounted to the head 24 (See FIGS. 8B and 9B).

Referring to FIGS. 3 and 5A-5C, the collet 150 preferably includes a first or upper end 152 sized and configured to contact at least a portion of the spinal rod 250 (schematically depicted in FIG. 5A) when the spinal rod 250 is received within a rod-receiving channel 208 formed in the body 200 and a second or lower end 154 sized and configured to contact at least a portion of the head portion 24 of the bone anchor 20. More preferably, the upper end 152 of the collet 150 includes a seat 160 sized and configured to receive at least a portion of the spinal rod 250 when the spinal rod 250 is received within the rod-receiving channel 208 of the body 200. The lower end 154 of the collet 150 preferably includes an interior cavity 165 for receiving and securing the head portion 24 of the bone anchor 20 so that, as will be generally appreciated by one of ordinary skill in the art, the bone anchor 20 can polyaxially rotate through a range of angles with respect to the collet 150 and hence with respect to the body 200. The cavity 165 formed in the collet 150 preferably has a curvate or semi-spherical shape for receiving the curvate or semi-spherical head portion 24 of the bone anchor 20 so that the bone anchor 20 can polyaxially rotate with respect to the collet 150 and hence with respect to the body 200. Furthermore, at least a portion of the outer surface of the collet 150 is comprised of a curvate or spherical, convex surface 151 having a radius of curvature r.sub.5 for contacting the inner surface 211 of the body 200, preferably the lower edge portion 218, as will be described in greater detail below.

The collet 150 preferably also includes one or more slots 170 (shown as a plurality of slots) extending from the lower end 154 thereof so that at least a portion of the collet 150 is: (i) radially expandable so that the head portion 24 of the bone anchor 20 can be inserted through the lower end 154 and into the cavity 165 of the collet 150 and (ii) radially compressible to compress or crush-lock against the head portion 24 of the bone anchor 20, in accordance with the application of radial forces applied thereto. In the preferred embodiment, the slots 170 define a plurality of flexible arms 172. Preferably each flexible arm 172 includes a root end 173 and a terminal end 174. The outer surface of the flexible arms 172 preferably include the curvate or spherical convex surface 151 of the collet 150 for defining a line-contact with the inner surface 211 of the body 200, preferably the first undercut 218a, as will be described in greater detail below.

The collet 150 may also include one or more grooves 175 formed on the outer surface thereof for engaging a projection or dimple 216a formed in the inner surface 211 of the body 200. As will be described in greater detail below, the collet 150 is permitted to float within the axial bore 206 formed in the body 200 between a loading position and a locked position. That is, the collet 150 is preferably movably positioned within the body 200 in an assembled configuration. Interaction between the one or more grooves 175 and the projection or dimples 216a prevents the collet 150 from moving out of the upper end 202 of the body 200 when in the loading position.

The collet 150 also includes a bore 156 extending from the upper end 152 to the lower end 154 with an upper opening at the upper end 152 so that, for example, a drive tool, such as, for example, a screw driver 500, can be inserted through the collet 150 and into engagement with the bone anchor 20 so that the bone anchor 20 may be rotated into engagement with the patient's vertebra 700. The upper opening at the upper end 152 of the collet 150 also permits simultaneous insertion of the screw driver 500 and a second tool, such as the sleeve 600, therethrough to engage the head 24 (FIGS. 8B and 9B).

The collet 150 may also include one or more provisional rod-locking features so that the spinal rod 250 may be provisionally coupled to the collet 150, and hence with respect to the body 200. The provisional rod-locking features may be any mechanism now or hereafter developed for such purpose.

Referring to FIG. 5C, the collet 150 includes one or more inwardly projecting ledges 184, 186 disposed on an inner surface 161 of the seat 160 adjacent the upper end 152 of the collet 150. The ledges 184, 186 may be engaged by a tool (not shown) to apply a force between the collet 150 and the body 200 to move the collet 150 relative to the body 200. For example, the body 200 may be urged downwardly toward the bone anchor 20 relative to the collet 150 when the collet 150, body 200 and bone anchor 20 are in the locked position. Such application of a force may move the collet 150 from the locked position into the loading position, in situ, such that the flexible arms 172 are able to flex outwardly within an enlarged diameter portion 220 to permit the head 24 to move out of the cavity 165. Accordingly, the ledges 184, 186 may be utilized to disassemble the collet 150 and body 200 from the bone anchor 20 after the collet 150 and body 200 have been locked to the head 24.

Referring to FIGS. 6A-6D and 7A-7B, the body 200 may generally be described as a cylindrical tubular body having a longitudinal axis 201, an upper end 202 having an upper opening 203, a lower end 204 having a lower opening 205, and an axial bore 206 substantially coaxial with the longitudinal axis 201 of the body 200. The axial bore 206 extends from the upper opening 203 to the lower opening 205. The axial bore 206 preferably has a first diameter portion $D_1$ proximate the upper end 202. The body 200 also includes a substantially transverse rod-receiving channel 208 (shown as a top loading U-shaped rod-receiving channel) defining a pair of spaced apart arms 209, 210. The inner surface 211 of the spaced apart arms 209, 210 preferably includes a plurality of threads 212 for engaging a locking cap 300. Alternatively, the body 200 and, in particular, the spaced apart arms 209, 210 may have nearly any mounting receiving structure for engaging the locking cap 300 including, but not limited to, external threads, cam-lock, quarter lock, clamps, etc. The outer surface 213 of the spaced apart arms 209, 210 may each include a recess 214 for engaging one or more surgical instruments such as, for example, rocker forceps, a compressor, a distractor, a sleeve, minimally invasive instrumentation, etc.

Referring to FIGS. 5A-6E, the axial bore 206 preferably has the first diameter portion $D_1$ proximate the upper end 202. The inner surface 211 of the axial bore 206 preferably also includes a lower end portion 218 proximate the lower end 204 thereof. The lower end portion 218 defines a second diameter portion $D_2$, which is comprised of the smallest diameter portion of the axial bore 206. The second diameter portion $D_2$ is preferably defined by a first spherical undercut 218a adjacent the lower end 204 of the body 200. The first spherical undercut 218a preferably has a second radius of curvature r2 that is centered on the longitudinal axis 201 of the body 200. The second diameter portion $D_2$ is preferably smaller than the first diameter portion $D_1$ of the axial bore 206 such that the collet 150 may be inserted through the upper end 202 into the axial bore 206, but generally preventing the collet 150 from being inserted into the lower end 204 or from falling out of the lower end 204 once inserted into the axial bore 206.

The first spherical undercut 218a is preferably defined as a curvate or spherical concave surface for accommodating the outer curvate or spherical convex surface 151 of the collar 150. The first spherical undercut 218a and the spherical convex surface 151 preferably have a different radius of curvature such that line contact is defined between the surfaces 151, 218 when the collet 150 is positioned proximate the lower end 204. The second diameter portion $D_2$ is preferably sized and configured so that the enlarged head portion 24 of the bone anchor 20 may be passed through the lower opening 205 of the body 200, but is prevented from passing therethrough once the head portion 24 of the bone anchor 20 is received within the interior cavity 165 of the collar 150.

The inner surface 211 of the axial bore 206 preferably includes an enlarged portion 220 that is located toward the lower end 204 relative to the first diameter portion $D_1$. The enlarged portion 220 preferably defines a third diameter $D_3$ comprised of a curvate, preferably spherical, radially outwardly recessed portion. In the enlarged portion 220 of the axial bore 206, the third diameter $D_3$ is larger than the first diameter $D_1$ of the axial bore 206. In addition, the third diameter $D_3$ is larger than the second diameter $D_2$. In the preferred embodiment, the third diameter $D_3$ is defined by a second spherical undercut 220a.

The enlarged portion 220 is preferably located in between the upper end 202 and the lower end portion 218 and accommodates expansion of the flexible arm 172 therein when the head 24 is loaded into the collet 150, as will be described in greater detail below. The enlarged portion 220 is preferably in the form of a curvate or spherical concave surface having a third radius of curvature r3, which defines the third diameter $D_3$ at the largest diameter within the axial bore 206. The third radius of curvature r3 defines the spherical nature of the second spherical undercut 220a. The enlarged portion 220 is sized and configured so that when the collet 150 is placed in general alignment with the curvate or spherical concave surface of the enlarged portion 220, the flexible arms 172 of the collet 160 are permitted to radially expand within the axial bore 206 of the body 200 so that the head portion 24 of the bone anchor 20 can be inserted through the lower opening 205 formed in the body 200 and into the cavity 165 formed in the collet 150. More preferably, the enlarged portion 220 is sized and configured so that the outer curvate or spherical convex surface 151 of the collet 150 does not touch or contact the enlarged portion 220 of the body 200 when the head 24 is loaded into the collet 150. That is, the enlarged portion 220 formed in the body 200 is preferably sized and configured so that a gap remains between the outer curvate or spherical convex surface 151 of the collet 150 and the enlarged portion 220 of the body 200 even when the flexible arms 172 radially expand to accept the head portion 24 of the bone anchor 20. The enlarged portion 220 is not limited to constructions comprised of the preferred curvate or spherical undercut defined by the third radius of curvature r3 and may be constructed of nearly any undercut having nearly any shape that permits expansion of the collet 150 therein in the loading position to accept the head 24. For example, the enlarged portion 220 may be defined by a rectangular slot or groove on the inner surface 211 that results in the third diameter $D_3$ being larger than the first and second diameters $D_1$, $D_2$.

In the preferred embodiment, the second radius of curvature r2 of the first spherical undercut 218a is preferably different than an outer radius of curvature r5 of the outer curvate or spherical convex surface 151 of the collet 150 so a line contact results between the first spherical undercut 218a and the outer convex surface 151 when the collet 150 is positioned adjacent the lower end portion 218. That is, by providing non-matching radius of curvatures between the first spherical undercut 218a and the collet 150, only line contact occurs between the first spherical undercut 218a of the body 200 and the outer curvate or spherical convex surface 151 of the collet 150. The line contact between the body 200 and the collet 150 effectively pinches the lower ends of the flexible arms 172 onto the lower end of the head 24 below the greatest diameter of the head 24 to direct the lower end 154 beneath the largest diameter of the head 24, effectively locking the bone anchor 20 to the collet 150 in the locked position. In addition, the line contact between the collet 150 and body 200 permits disengagement of the collet 150 from the body 200 after the collet 150 and body 200 are engaged in the locked position or popping-off of the body 200 and collet 150 from the bone anchor 20, in situ.

Referring to FIGS. 5A-5C, 6F and 6G, the second and third diameters $D_2$, $D_3$ may be formed by a single internal radius of curvature r4 that undercuts the body 200 in the axial bore 206. The single internal radius of curvature r4 preferably permits expansion of the collet 150 to accept the head 24, insertion of the collet 150 into the axial bore 206 from the upper end 202 but not the lower end 204 and line contact between the outer curvate or spherical convex surface 151 of the collet and the lower end portion 218 when the collet 150 is in facing engagement with the lower end portion 218. In this configuration, the second diameter portion $D_2$ is smaller than the first diameter portion $D_1$, which is smaller than the third diameter portion $D_3$.

Referring to FIGS. 1-3 and 5A-6C, the body 200 and collet 150 also preferably include a collet retention feature 50 so that once the collet 150 has been inserted into the bore 206 formed in the body 200 and, if necessary, the collet retention feature 50 has been engaged, the collet retention feature 50 inhibits the collet 150 from passing back through the upper opening 203 formed in the body 200, but permits some degree of vertical translation or floating of the collet 150 with respect to the body 200. That is, once inserted into the axial bore 206 of the body 200, the collet 150 is sized and configured to float or move within the axial bore 206 between a loading position and a locking position. The collet retention feature 50 preferably prevents the collet 150 from moving out of the upper opening 203 of the body 200. Preferably the collet retention feature 50 permits the flexible arms 172 to align with the enlarged portion 220 in the loading position when the lower edge of the grooves 175 come into contact with the dimples 216a. In addition, the collet 150 is preferably permitted to float between the loading position and the locking position prior to locking of the head 24 in the collet 150. Specifically, the collet 150 may float between the loading position where the dimples 216a are in contact with the lower edge of the grooves 175 and the locking position wherein the outer curvate or spherical convex surface 151 is in line contact with the lower end portion 218. The collet retention feature 50 preferably limits rotation of the collet 150 with respect to the body 200, because the dimples 216a slide within the grooves 175, so that the seat 160 formed in the collet 150 is aligned with the rod-receiving channel 208 formed in the body 200. However, the retention feature 50 is not limited to limiting rotation of the collet 150 with respect to the body 200 and may be configured to permit unlimited rotation of the collet 150 relative to the body 200 by eliminating the grooves 175 from the collet 150 and forming a shelf (not shown) around the collet 150 at the bottom end of the grooves 175 such that the dimples 216a engage the shelf to limit removal of the collet 150 out of the upper end 202 of the body 200, but permit unlimited rotation of the collet 150 relative to the body 200 in the assembled configuration.

The collet retention feature 50 may be any feature now or hereafter known for such purpose including, but not limited to, for example, an inwardly protruding shoulder or detent formed on the collet 150 for engaging corresponding indentations formed on the inner surface 211 of the body 200. In the preferred embodiment, the body 200 includes one or more partial passageways 216 formed therein so that once the collet 150 has been received within the axial bore 206 of the body 200, a force may be applied to the partial passageways 216 formed in the body 200 deforming the remaining portion of the partial passageway 217 into the dimple or projection 216a formed in the inner surface 211 of the body 200. That is, once the collet 150 has been received within the bore 206 of the body 200, an external force may be applied to the partial passageways 216 formed in the body 200 transforming the passageways 216 into the projections or dimples 216a that extend inwardly from the inner surface 211 of the spaced apart arms 209, 210 and into the bore 206 formed in the body 200. The dimples or projections 216a are preferably sized and configured to interact with the longitudinal groove 175 formed in the outer surface of the collet 150 so that the collet 150 is permitted to move with respect to the body 200 at least along the longitudinal axis 201, but inhibited from moving back through the upper opening 203 formed in the body 200. The collet 150 is also preferably partially inhibited from rotational movement with respect to the body 200. Movement of the collet 150 with respect to the body 200 toward the upper end 202 is preferably inhibited by the projections or dimples 216a contacting the bottom and/or lateral surfaces of the grooves 175. Limiting rotational movement of the collet 150 with respect to the body 200 permits alignment of the rod-receiving channel 208 and the seat 160 for receiving the rod 250, as will be described in greater detail below.

In use, positioning the collet 150 in general alignment with the curvate or spherical concave surface of the enlarged portion 220 in the loading position preferably enables the flexible arms 172 of the collet 150 to radially expand within the axial bore 206 of the body 200 so that the head portion 24 of the bone anchor 20 can be inserted through the lower opening 205 formed in the body 200 and into the cavity 165 formed in the collet 150. The enlarged portion 220 formed in the body 200 is preferably sized and configured so that a gap remains between the outer curvate or spherical convex surface 151 of the collet 150 and the enlarged portion 220 of the body 200 even when the flexible arms 172 radially expand to accept the head portion 24 of the bone anchor 20. Thereafter, movement of the collet 150 into general alignment and engagement with the first spherical undercut 218a of the lower end portion 218 causes a radial inward force to be applied to the flexible arms 172, which in turn causes the flexible arms 172 to compress against the head portion 24 of the bone anchor 20, thereby securing the position of the bone anchor 20 with respect to the collet 150 and hence with respect to the body 200. The lower end portion 218 and the outer curvate or spherical convex surface 151 of the collet 150 have non-matching radii of curvature r2, r4, r5 so that only line contact occurs between these components.

The head portion 24 of the bone anchor 20 and interaction of the dimples 216 with the grooves 175 preferably moves the collet 150 into alignment with the enlarged portion 220 as the head portion 24 is inserted through the lower opening 205 and into the axial bore 206. Moreover, the collet 150 is preferably moved into alignment and engagement with the lower edge portion 218 via engagement of the locking cap 300, as will be described in greater detail below.

Referring to FIGS. 7A and 7B, the locking cap 300 is preferably an externally threaded set screw 302 for threadably engaging the threads 212 formed on the inner surface 211 of the body 200. The externally threaded set screw 302 generally provides flexibility when inserting a spinal rod 250 into the body 200 such that the spinal rod 250 does not have to be completely reduced or seated within the body 200 prior to engagement of the cap 300. Incorporation of a threaded set screw 302 also enables the set screw 302 to reduce the spinal rod 250 during tightening of the locking cap with respect to the body 200. The locking cap 300 may be any locking cap now or hereafter developed for such purpose including, but not limited to, an externally threaded cap, a quarter-turn or partial-turn locking cap, two-piece set screw, etc.

As shown, the externally threaded set screw 302 preferably includes a drive surface 304 for engaging a corresponding drive tool for securing (e.g., threading) the set screw 302 onto the body 200. The drive surface 304 may take on any form now or hereafter developed for such purpose, including, but not limited to, an external hexagon, a star drive pattern, a Phillips head pattern, a slot for a screw driver, a threading for a correspondingly threaded post, etc. The drive surface 304 is preferably comprised of an internal recess. The specific shape of the internal recess may be chosen to cooperate with the corresponding drive tool. The drive surface 304 may also be configured to include the first and second tool interfaces 40, as were described above.

The externally threaded set screw 302 preferably also includes a saddle 310 operatively coupled thereto. The saddle 310 includes a transverse recess 312 formed therein for contacting at least a portion of the spinal rod 250. The rod-contacting surface of the recess 312 may include a surface finish (not shown) that adds roughness, such as, for example, a knurl, bead blasting, grooves, or other textured finish that increases surface roughness and enhances rod push through strength.

The saddle 310 may be coupled to the set screw 302 by any means now or hereafter developed for such purpose including, but not limited to, adhesion, mechanically fastening, etc. The set screw 302 preferably includes a bore 306 for receiving a stem 316 formed on a top surface 311 of the saddle 310. In use, the saddle 310 is preferably coupled to the set screw 302 but is free to rotate with respect to the set screw 302 so that the saddle 310 can self-align with the spinal rod 250 while the set screw 302 is being rotated with respect to the body 200.

In one particularly preferred embodiment, the threads formed on the externally threaded set screw 302 may incorporate inclined load flanks forming an angle with respect to the longitudinal axis 201 of the body 200. The load flanks may be converging so that the top surface of the thread and the bottom surface of the thread converge. The angle may be about five degrees (5.degree.), although, as will be generally appreciated by one of ordinary skill in the art, the threads may take on any other form now or hereafter known for such purpose including, negative load threads, perpendicular threads flanks, buttress threads, etc.

Referring to FIGS. 1-7B, the polyaxial bone fixation element 10 is preferably provided to the user in a kit including at least (1) bone anchors, (2) locking caps, and (3) pre-assembled collet/body subassemblies. The pre-assembled collet/body subassemblies are preferably assembled by inserting the collet 150 into the axial bore 206 formed in the body 200 through the upper opening 203 formed in the body 200. The flexible arms 172 may flex inwardly as the collet 150 is inserted into the axial bore 206, if the greatest diameter of the flexible arms 172 is larger than the first diameter $D_1$. Such a configuration generally results in the collet 150 being retained within the axial bore 206, even before the collet retention feature 50 is engaged. Once the collet 150 is positioned within the axial bore 206 such that the flexible arms 172 are positioned proximate the enlarged portion 220, a force is applied to a distal end of the partial passageway 216 formed in the body 200 so that a projection or dimple 216a is formed, which extends into the bore 206 of the body 200. The projection or dimple 216a is positioned within the longitudinal groove 175 formed in the collet 150 so that the collet 150 is free to vertically translate or float within the bore 206 with respect to the body 200, but generally prevented from passing back up through the upper opening 203 formed in the body 200 and limited in its ability to rotate relative to the body 200.

The kit is preferably shipped to the user for use in spinal surgery. During surgery, the surgeon preferably identifies a level of the spine where the surgery will take place, makes and incision to expose the selected area and implants the bone anchors 20 into the desired vertebrae 700. The body/collet subassemblies are preferably popped-on to the bone anchors 20 by urging the head 24 through the lower opening 205. Accordingly, the collet/body subassembly may be engaged with the head portion 24 of the bone anchor 20 in situ. Specifically, as the head 24 moves into the lower opening 205, the collet 150 is urged toward and into the loading position wherein the lower end of the longitudinal grooves 175 contact the dimples 216a. In the loading position, the outer curvate or spherical convex surface 151 of the collet 150 is in general vertical alignment with the enlarged curvate or spherical concave surface of the enlarged portion 220 formed in the axial bore 206 of the body 200. Alignment of the enlarged portion 220 with the collet 150 enables the collet 150 to radially or outwardly expand so that the head portion 24 of the bone anchor 20 can be received within the cavity 165 formed in the collet 150.

Once the head 24 is positioned in the cavity 165, the head portion 24 of the bone anchor 20 and the collet 150 are both preferably constrained within the body 200. The bone anchor 20 is preferably able to polyaxially rotate with respect to the collet 150 and the body 200 in this configuration. The spinal rod 250 is inserted into the rod-receiving channel 208 formed in the body 200 and onto the inner surface 161 of the seat 160. The spinal rod 250 is preferably positioned in facing engagement with the inner surface 161 of the seat 160. The set screw 302 is preferably threaded into engagement with the threads 212 formed in the body 200 to urge the spinal rod 250 and collet 150 toward the lower end 204.

Rotation of the set screw 302 causes the bottom surface of the set screw 300, preferably the saddle 310, to contact the top surface of the spinal rod 250, which in turn causes the spinal rod 250 and the collet 150 to move downwards with respect to the body 200. Downward movement of the collet 150 with respect to the body 200 causes line contact between the outer curvate or spherical convex surface 151 of the collet 150 and the first spherical undercut 218a of the lower end portion 218. Additional tightening of the set screw 300 and downward movement of the spinal rod 250 and collet 150 results in an inwardly directed compressive force to the flexible arms 172, causing the flexible arms 172 to pivot inwardly toward the head portion 24 at their terminal ends 174 about the root ends 173. In a locking position, the flexible arms 172 engage the head 24 of the bone anchor 20 securing the position of the bone anchor 20 with respect to the collet 150 and the body 200. Specifically, the flexible arms 172 of the collet 150 radially compress against the head portion 24 of the bone anchor 20, which secures the position of the bone anchor 20 with respect to the body 200. The line contact between the collet 150 and body 200 proximate the terminal ends 174 direct the radial inward force on the flexible arms 172 at a location preferably below the largest diameter of the head 24 to efficiently urge the terminal ends 174 beneath the curved outer surface of the head 24 in the locked position. In addition, the spinal rod 250 is sandwiched between the set screw 302 and the collet 150 in the locking position, thereby securing the position of the spinal rod 250 with respect to the body 200 and the bone anchor 20.

Referring to FIGS. 3 and 5A-6E, the collet 150 and body 200 may be popped-off of the bone anchor 20, in situ, after the bone fixation element 10 is engaged in the locked configuration. Specifically, the set screw 300 may be removed from the body 200 and the spinal rod 250 may be extracted from the rod-receiving channel 208 and the seat 160. A tool (not shown) engages the ledges 184, 186 and the body 200 and applies a force between the collet 150 and the body 200 to move the body 200 downwardly toward the body anchor 20. The line contact between the body 200 and the collet 150 is released and the collet 150 is urged into the loading position. In the loading position, the flexible arms 172 flex outwardly within the enlarged portion 220 to permit popping-off of the body 200 and collet 150 from the head 24 of the bone anchor 20. The collet 150 and body 200 may then be popped back onto the bone anchor 20.

Referring to FIGS. 4A, 4B and 8A-9B, the head portion 24 of the bone anchor 20 preferably includes a drive surface 30 in the form of an internal drive recess or a first tool interface 32 and a second tool interface 40. The second tool interface 40 preferably includes a plurality of threads 42 for threadably engaging the sleeve 600. The sleeve 600 preferably accommodates a variety of surgical instruments now or hereafter known including, but not limited to, the screw driver 500, a fluid delivery device such as the injection assembly 650, a compressor, a distractor, minimally invasive instrumentation, etc. By incorporating the second tool interface 40 into the head portion 24 of the bone anchor 20, the surgical instruments are able to directly engage the bone anchor 20, thus eliminating the need for the surgical instruments and/or the sleeve 600 to engage the body 200 or collet 150 of the polyaxial bone fixation element 10. In addition, once the sleeve 600 is engaged with the second tool interface 40, toggling between the screw driver 500 or another instrument inserted through an internal bore in the sleeve 600 and the bone anchor 20 is limited. In the preferred embodiment, the sleeve 600 is utilized to draw the screw driver 500 into the first tool interface 32 to limit toggling between the screw driver 500 and the bone anchor 20. The second tool interface 40 is described herein as interacting or engaging the sleeve 600, but is not so limited and may be configured to interact or engage with nearly any tool or instrument that preferably is utilized to positively engage the head 24 and apply forces to the bone anchor 20 for manipulating the bone anchor 20, vertebra 700 mounted to the bone anchor 20 or any other structure that is mounted to the bone anchor 20.

In order to facilitate implantation of the polyaxial bone fixation elements 10 and to perform, for example, one or more steps in a surgical procedure, it is advantageous to limit or remove "toggling" between the polyaxial bone fixation elements 10 and any surgical instruments that are utilized with the bone fixation elements 10. By incorporating the second tool interface 40 into the head portion 24 of the bone anchor 20, the sleeve 600 and, indirectly, the surgical instrument, for example, the screw driver 500, are directly connected to the bone anchor 20. The sleeve 600 includes a threaded distal portion 602 for threadably engaging the threads 42 of the second tool interface 40. In this manner, the sleeve 600 is directly coupled and secured to the bone anchor 20. Through this engagement, toggling is limited between the sleeve 600 and the bone anchor 20. In addition, having a close tolerance between in internal surface of the bore in the sleeve 600 and the screw driver 500 or other instrument significantly limits toggling between the screw driver 500 or other instrument and the bone anchor 20.

During the surgical procedure, the direct connection of the sleeve 600 with the bone anchor 20 facilitates protection of the polyaxial locking mechanism (the collet 150 and the body 200) of the polyaxial bone fixation element 10 and provides a more stable distraction, because the forces applied to the sleeve 600 are transferred directly to the bone anchor 20 via the second tool interface 40 and into the vertebra 700, as opposed to acting through these elements as well as the collet 150 and/or the body 200, which may distort some of the forces and cause toggling. In addition, instruments, such as the screw driver 500 or the injection assembly 650 may be securely positioned in engagement with the bone anchor 20 to drive the bone anchor 20 with the screw driver 500, inject bone cement or other fluid into and through the bone anchor 20 or otherwise conduct a procedure with the bone anchor 2, without operating through the body 200 and/or collet 150.

The second tool interface 40 preferably does not obstruct access to the drive recess 32, because the second tool interface 40 is preferably located above and radially outwardly relative to the drive recess 32. However, the second tool interface 40 is not limited to being located above and radially outwardly relative to the drive recess or first tool interface 32 and may be located below and radially inwardly relative to the first tool interface 32, as long as tools or instruments are able to engage the first and second tool interfaces 32, 40 simultaneously. Specifically, the second tool interface 40 may be comprised of a threaded recess in the bone anchor 20 having a smaller diameter and located below the first tool interface 32. Moreover, as best shown in FIGS. 9A and 9B, the sleeve 600 preferably includes the longitudinal bore so that the screw driver 500, for example, may engage the drive recess 32 formed in the head portion 24 of the bone anchor 20. In this manner, the sleeve 600 engages the bone anchor 20 via the second tool interface 40 while the screw driver 500 simultaneously engages the drive recess 32.

Figure 8A:
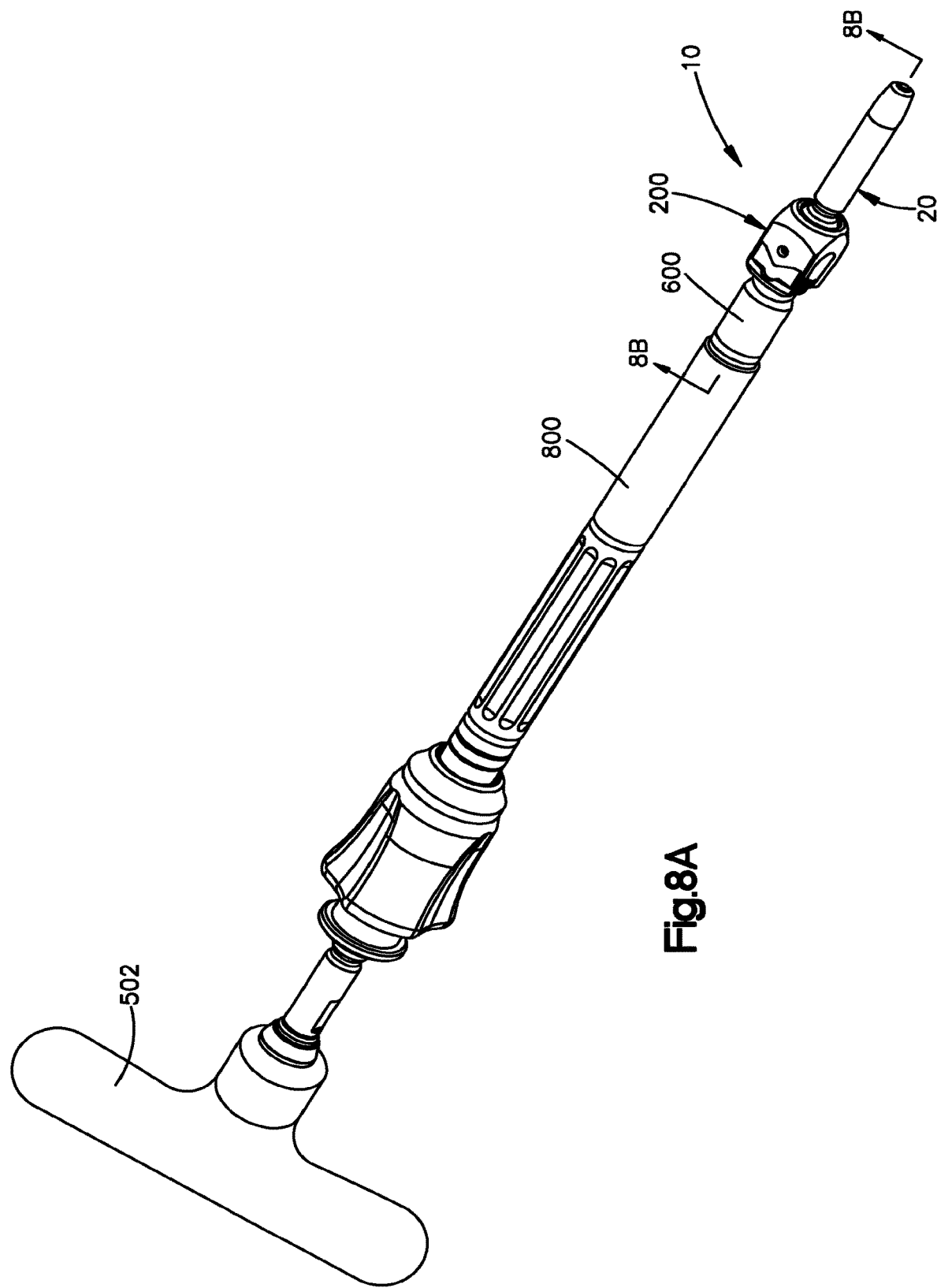
FIG. 8A illustrates a side perspective view of a preferred embodiment of a screw driver and a sleeve coupled to a portion of the polyaxial bone fixation element of FIG. 1.
Figure 8B:
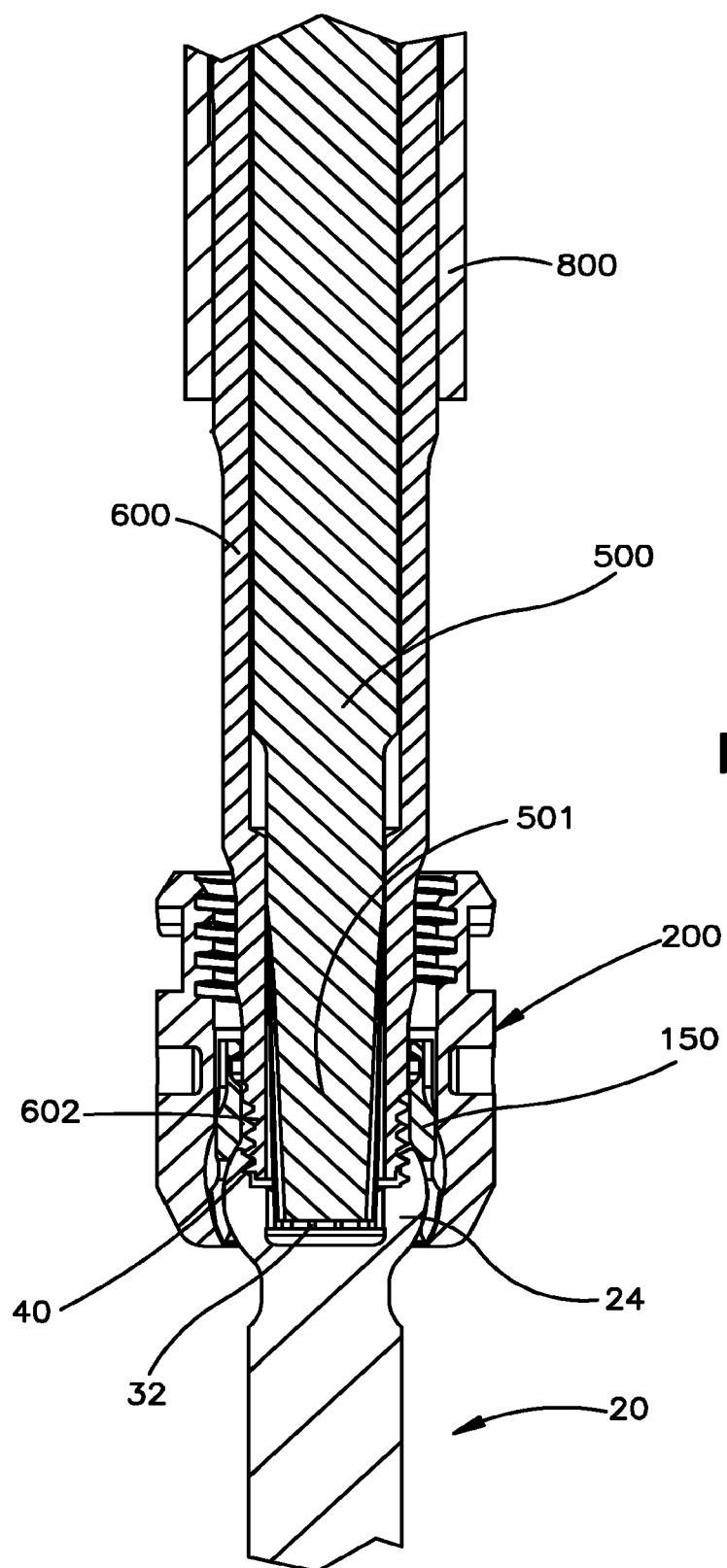
FIG. 8B illustrates a cross-sectional view of the screw driver and sleeve coupled to the portion of the polyaxial bone fixation element of FIG. 1, taken along line 8B-8B of FIG. 8A.
Figure 9B:
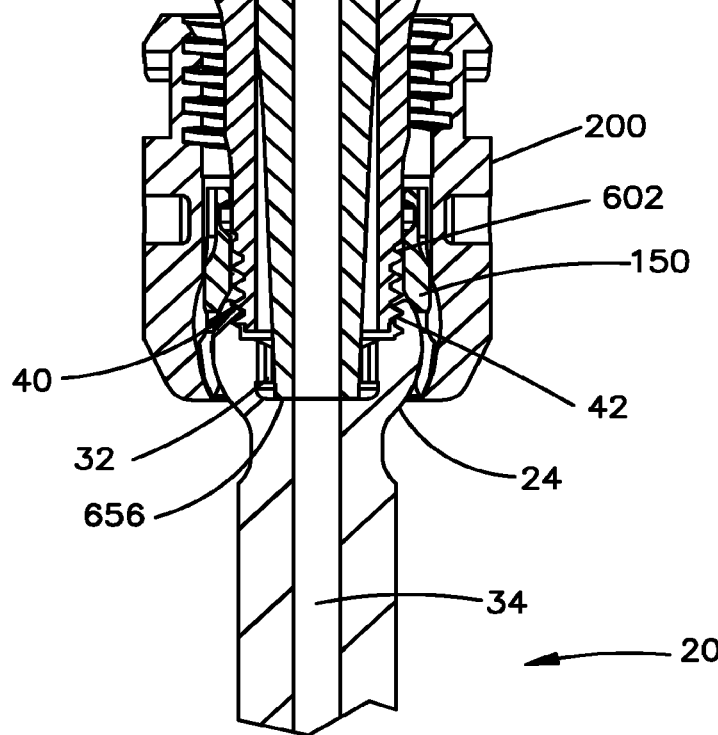
FIG. 9B illustrates a magnified, cross-sectional view of the syringe assembly and sleeve shown in FIG. 9A, taken from within the circle 9B of FIG. 9A.

Referring to FIGS. 8A and 8B, the sleeve 600 is preferably associated with a slip sleeve 800 that surrounds the sleeve 600 in a working configuration. The sleeve 600 and the screw driver 500 are rotatable relative to the slip sleeve 800 such that a surgeon may grasp the slip sleeve 800 while turning a handle 502 on a distal end of the screw driver 500 to screw the bone anchor 20 into or out of the vertebra 700. When the surgeon rotates the handle 502, the sleeve 600, screw driver 500 and bone anchor 20 each rotate relative to the slip sleeve 800.

In an anchor driving position (FIG. 8B), external threads 602 on the sleeve 600 are fully threaded into the threads 42 of the second tool interface 40, thereby limiting any toggling between the sleeve 600 and bone anchor 20. The top 501 of the screw driver 500 is also fully engaged with the drive recess 32 of the bone anchor 20 in the anchor driving position. When a surgeon has completed manipulating the bone anchor 20 with the screw driver 500, the screw driver 500 may be removed from the sleeve 600 and another instrument may be utilized with the sleeve 600 to gain access to the bone anchor 20.

Referring to FIGS. 9A and 9B, the injection assembly 650 may be utilized with the sleeve 600 to inject bone cement or other flowable materials into a cannulated bone anchor 20'. Once the bone anchor 20' is mounted in the vertebra 700 and the sleeve 600 is mounted on the bone anchor 20', a cannula 652 of the injection assembly 650 is inserted into the sleeve 600. The cannula 652 is associated with a syringe 654 at a proximal end and includes a blunt tip 656 at a distal end. The cannula 652 preferably includes an engagement mechanism 656 proximate the proximal end to engage a proximal end of the sleeve 600 to secure the cannula 652 to the sleeve 600. In addition, the engagement mechanism 656 preferably urges the blunt tip 656 of the cannula 652 into engagement with a shelf 32a at the bottom of the first tool interface 32 such that a flow channel 34 of the cannula 652 is in communication with a flow channel 652a of the cannula and a seal is created between the blunt tip 656 and the shelf 32a. In the preferred embodiment, the engagement mechanism 656 is comprised of a threaded joint that may be tightened to secure the cannula 652 relative to the sleeve 600 and securely seal the blunt tip 656 to the shelf 32a, thereby generally preventing leakage of bone cement or other flowable fluid into the first tool interface 32. Bone cement is preferably injected into the flow channel 652a with the injection assembly 650 and into the vertebra 700 to securely mount the bone anchor 20' to the vertebra 700, particularly in generally weak, brittle and/or osteoporotic bone. The bone anchor 20' may also be fenestrated to inject bone cement toward the sides of the bone anchor 20' or to generally directionally dispense the bone cement or other fluid. Further, the bone anchor 20' may be utilized to extract material from the vertebra 700 or other bone that the bone anchor 20' is engaged with by drawing the material into the flow channel 652a, by, for example, creating a vacuum in the flow channel 652a. For example, the bone anchor 20' may be utilized to extract bone marrow from the bone. Further, the bone anchor 20' may be utilized to aid in bone graft extension, as would be apparent to one having ordinary skill in the art.

It should be understood that while the bone anchor 20 is being described herein as preferably including the second tool interface 40, the second tool interface 40 is optional. Furthermore, it should be understood that the bone anchor 20 including the second tool interface 40 may be used in any other type of bone screw application such as, for example, long bone fixation, fracture fixation, or in connection with securing a bone plate, vertebral spacer, dental implant, etc.

The polyaxial bone fixation element 10 including the bone anchor 20, the collet 150, the body 200 and the locking cap 300 may be made from any biocompatible material now or hereafter known including, but not limited to, metals such as, for example, titanium, titanium alloys, stainless steel, Nitinol, etc.

As will be appreciated by those skilled in the art, any or all of the components described herein may be provided in sets or kits so that the surgeon may select various combinations of components to perform a fixation procedure and create a fixation system which is configured specifically for the particular needs/anatomy of a patient. It should be noted that one or more of each component may be provided in a kit or set. In some kits or sets, the same device may be provided in different shapes and/or sizes.

While the foregoing description and drawings represent the preferred embodiment of the present invention, it will be understood that various additions, modifications, combinations and/or substitutions may be made therein without departing from the spirit and scope of the present invention as defined in the accompanying claims. In particular, it will be clear to those skilled in the art that the present invention may be embodied in other specific forms, structures, arrangements, proportions, and with other elements, materials, and components, without departing from the spirit or essential characteristics thereof. One skilled in the art will appreciate that the invention may be used with many modifications of structure, arrangement, proportions, materials, and components and otherwise, used in the practice of the invention, which are particularly adapted to specific environments and operative requirements without departing from the principles of the present invention. In addition, features described herein may be used singularly or in combination with other features. The presently disclosed embodiments are, therefore, to be considered in all respects as illustrative and not restrictive, the scope of the invention being indicated by the appended claims and not limited to the foregoing description.

It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention, as defined by the appended claims.

What is claimed:

1. A body for interconnecting a bone anchor and a longitudinal spinal rod, the body including:
   an upper end that defines an upper opening;
   a lower end that defines a lower opening, wherein the body is elongate along a first longitudinal axis;
   a bore that extends between the upper opening and the lower opening along the first longitudinal axis, the bore defining a rod-receiving channel configured to receive the spinal rod, the rod-receiving channel disposed along a channel axis that is oriented substantially perpendicular to the first longitudinal axis, the bore at least partially defined by a first curved surface that forms a first curved undercut having a first body diameter, and the bore at least partially defined by a second curved surface that forms a second curved undercut having a second body diameter that is larger than the first body diameter, the first curved surface positioned closer to the lower opening with respect to a direction parallel to the longitudinal axis than the second curved surface is to the lower opening with respect to the direction;
   the body further including a collet retention feature positioned at a fixed location between the upper opening and the second curved surface such that the collet retention feature is configured to inhibit movement of a collet that is between the collet retention feature and the lower opening from passing through the upper opening, the collet retention feature defining a retention opening having a third body diameter, and the lower opening defining a fourth body diameter;
   wherein the third body diameter is greater than the fourth body diameter and less than the second body diameter.

2. The body of claim 1, wherein the first curved undercut is a first spherical undercut, and wherein the second curved undercut is a second spherical undercut.

3. The body of claim 1, further including one or more partial passageways formed therein so that the body is configured to receive a force applied to the one or more partial passageways that deforms the one or more partial passageways into one or more dimples that extend into the bore of the body, whereby the one or more dimples would comprise the collet retention feature.

4. The body of claim 1, further including one or more dimples that comprise the collet retention feature.

5. The body of claim 1, wherein the upper opening of the body defines a fifth body diameter that is larger than the first body diameter, and smaller than the second body diameter.

6. An assembly configured to couple a spinal rod to a vertebra, the assembly comprising:
   the body of claim 1; and
   the bone anchor, which is elongate along a second longitudinal axis, the bone anchor including a head portion, a shaft portion, and a neck portion positioned between the head portion and the shaft portion, the head portion defining a first screw diameter measured perpendicular to the second longitudinal axis, the shaft portion defining a second screw diameter measured perpendicular to the second longitudinal axis, and the neck portion defining a third screw diameter perpendicular to the second longitudinal axis,
   wherein the third screw diameter is less than both the first screw diameter and the second screw diameter, the first screw diameter is less than both the first body diameter and the second body diameter.

7. The assembly of claim 6, wherein the head portion includes a first tool interface configured to engage a first surgical instrument, and the head portion includes a second tool interface configured to engage a second surgical instrument, the first tool interface and the second tool interface positioned in a head interface cavity.

8. The assembly of claim 7, wherein the first tool interface includes a drive surface which is an internal surface formed in the head portion of the bone anchor, the first tool interface is configured to receive an external tip of the first surgical instrument, and the second tool interface includes a plurality of threads formed on the head portion, the plurality of threads configured to threadedly engage a portion of the second surgical instrument.

9. The assembly of claim 7, wherein the second tool interface is located proximal of the first tool interface so that the second tool interface does not obstruct access to the first tool interface.

10. The assembly of claim 6, further comprising:
    the collet, the collet defining a cavity configured to receive the head portion of the bone anchor, the collet including a portion that is expandable and configured to facilitate entry of the head portion of the bone anchor into the cavity.

11. The assembly of claim 10, further comprising:
    a locking cap removably engageable with the body such that the locking cap is movable from an unlocked position to a locked position, wherein movement of the locking cap from the unlocked position to the locked position urges the spinal rod against the collet to secure the bone anchor relative to the body.

12. An assembly configured to couple a spinal rod to a vertebra, the assembly comprising:
    the body of claim 1; and
    the collet, the collet defining a cavity configured to receive the head portion of the bone anchor, and the collet including a portion that is expandable and configured to facilitate entry of the head portion of the bone anchor into the cavity.

13. The assembly of claim 12, wherein the collet is configured to move within the bore along the longitudinal axis from a loading position to a locked position, when the collet is in the loading position the head portion of the bone anchor is movable within the cavity relative to the collet, and when the collet is in the locked position the head portion of the bone anchor is unable to move within the cavity relative to the collet.

14. The assembly of claim 13, wherein the collet includes a first end, a second end and at least two slots extending from the second end, the at least two slots defining flexible arms that each have a root end, a terminal end and an outer curvate convex surface proximate the terminal end, wherein the flexible arms are positioned proximate the second curved surface in the loading position, and at least a portion of the outer curvate convex surface of the flexible arms are in line contact with at least a portion of the first curved surface in the locked position.

15. The assembly of claim 12, wherein the collet retention feature contacts a bottom end of a groove in the collet in the loading position to align the flexible arms with the second spherical undercut.

16. The assembly of claim 12, wherein the body includes one or more partial passageways formed therein so that once the collet has been received within the bore of the body, the body is configured to receive a force applied to the one or more partial passageways that deforms the one or more partial passageways into one or more dimples that extend into the bore of the body, and the one or more dimples comprise the collet retention feature.

17. The assembly of claim 16, wherein the one or more dimples interact with the collet to inhibit the collet from moving back through the upper opening formed in the body.

18. The assembly of claim 12, wherein the first curved surface defines a first radius of curvature as measured in a plane, the portion of the collet that is expandable includes an outer collet surface configured to abut the first curved surface, the outer collet surface defines a second radius of curvature as measured in the plane, and the first radius of curvature is different than the second radius of curvature.

19. An assembly configured to couple a spinal rod to a vertebra, the assembly comprising:
the body of claim 1; and
a set screw and a saddle, the set screw configured to threadedly engage with the upper end of the body, the saddle coupled to the set screw such that the set screw is free to rotate with respect to the saddle.

20. A body for interconnecting a bone anchor and a longitudinal spinal rod, the body including:
an upper end that defines an upper opening;
a lower end that defines a lower opening, wherein the body is elongate along a first longitudinal axis;
a bore that extends between the upper opening and the lower opening along the first longitudinal axis, the bore defining a rod-receiving channel configured to receive the spinal rod, the rod-receiving channel disposed along a channel axis that is oriented substantially perpendicular to the first longitudinal axis, the bore at least partially defined by a first curved surface that forms a first curved undercut having a first body diameter, and the bore at least partially defined by a second curved surface that forms a second curved undercut having a second body diameter that is larger than the first body diameter, the first curved surface positioned closer to the lower opening with respect to a direction parallel to the longitudinal axis than the second curved surface is to the lower opening with respect to the direction;
the body further including a collet retention feature positioned at a fixed location between the upper opening and the second curved surface such that the collet retention feature is configured to inhibit movement of a collet that is between the collet retention feature and the lower opening from passing through the upper opening, the collet retention feature defining a retention opening having a third body diameter, the third body diameter measured from a first point on a surface of the collet retention feature to a second point on the surface of the collet retention feature, the first point facing the second point, and the lower opening defining a fourth body diameter;
wherein the third body diameter is greater than the fourth body diameter.

* * * * *